United States Patent
Hwang et al.

(10) Patent No.: US 7,405,043 B2
(45) Date of Patent: Jul. 29, 2008

(54) RESPONSIVENESS TO THERAPY FOR LIVER DISORDERS

(75) Inventors: Yuchi Hwang, Taipei (TW); Kuang-Den Chen, Taipei (TW); Chingwei Chang, Taipei (TW); Jui-Lin Chen, Taoyuan (TW); Ding-Shinn Chen, Taipei (TW); Pei-Jer Chen, Taipei (TW); Ming-Yang Lai, Taipei (TW)

(73) Assignee: Vita Genomics, Inc., Taipei (TW)

( * ) Notice: Subject to any disclaimer, the term of this patent is extended or adjusted under 35 U.S.C. 154(b) by 172 days.

(21) Appl. No.: 10/880,315

(22) Filed: Jun. 29, 2004

(65) Prior Publication Data

US 2005/0288497 A1    Dec. 29, 2005

(51) Int. Cl.
    *C12Q 1/68*    (2006.01)
(52) U.S. Cl. ......................................................... 435/6
(58) Field of Classification Search ........................ None
    See application file for complete search history.

(56) References Cited

U.S. PATENT DOCUMENTS

| | | | |
|---|---|---|---|
| 6,667,155 B2 | 12/2003 | Hijikata et al. | 435/6 |
| 2002/0119468 A1 | 8/2002 | Rosen | 435/6 |
| 2002/0127558 A1 | 9/2002 | Hijikata et al. | 435/6 |
| 2002/0192682 A1 | 12/2002 | Escary | 435/6 |
| 2003/0032090 A1 | 2/2003 | Hardiman et al. | 435/69.1 |
| 2003/0050269 A1 | 3/2003 | Escary | 514/44 |
| 2003/0087816 A1 | 5/2003 | Vermet et al. | 514/12 |
| 2003/0119010 A1 | 6/2003 | Powell et al. | 435/6 |
| 2003/0124524 A1 | 7/2003 | Kornman et al. | 435/6 |
| 2003/0148336 A1 | 8/2003 | Matsuyama et al. | 435/6 |
| 2003/0148972 A1 | 8/2003 | Thomas et al. | 514/44 |
| 2003/0224486 A1 | 12/2003 | Carman et al. | 435/69.5 |
| 2004/0043379 A1 | 3/2004 | Hashimoto et al. | 435/5 |
| 2004/0043402 A1 | 3/2004 | Meritet et al. | 435/6 |

*Primary Examiner*—James Martinell
(74) *Attorney, Agent, or Firm*—Fish & Richardson P.C.

(57) ABSTRACT

Sets of nucleic acids and methods for predicting a subject's responsiveness to therapy for liver disorders.

4 Claims, No Drawings

RESPONSIVENESS TO THERAPY FOR LIVER DISORDERS

BACKGROUND

Liver disorders, such as hepatitis, are major public health concerns. For example, hepatitis C is estimated to affect 200 million people worldwide. Patients with liver damage resulting from hepatitis C may develop chronic liver diseases, such as cirrhosis and hepatocellular carcinoma. Hepatitis C can be treated with interferon α and ribavirin. However, interferon α or ribavirin therapy causes significant side effects and is expensive. More importantly, only about 50% hepatitis C patients are responsive to the treatment. New therapies have been vigorously sought. Although several drug candidates are now being evaluated, the progress is rather slow due to a lack of appropriate systems for determining a patient's response to new therapies. Thus, there is a need for a reliable system and method for predicting a patient's response to treatment of hepatitis C and other liver disorders.

A patient's response to viral therapy is associated with various viral factors, e.g., the viral level, viral genotype, and mutation in certain viral proteins, and host factors, e.g., the patient's age, gender, race, host immune response, HLA alleles, and other genetic compositions, such as polymorphisms.

Single nucleotide polymorphisms (SNPs), a set of single nucleotide variants at genomic loci, are distributed throughout a genome. An SNP can be "allelic." More specifically, due to polymorphism, some members of a species have the unmutated sequence (i.e., the wild-type allele) and others have a mutated sequence (i.e., the mutant allele). In humans, a polymorphism or a set of polymorphisms may be associated with a genetic disorder. In addition, patients having different SNP genotypes respond to the same treatment differently. Therefore, an SNP genotype of a patient is expected to provide individualized guidance for preventing and treating various human disorders.

SUMMARY

This invention relates to sets of target nucleic acids, primers, and methods that can be used to predict the responsiveness of a subject to a therapy for treating hepatitis C and other liver disorders. The target nucleic acids contain one or more SNPs. The primers can be used in polymerase chain reaction (PCR) amplification for obtaining sequences containing the SNPs or can be used in single-base-extension for SNP typing.

Accordingly, one aspect of this invention features a set of SNP-containing target nucleic acids that include one or more of (i) a first target nucleic acid obtained from amplification of the human Adenosine Deaminase-RNA-specific (ADAR) gene nucleic acid template with a first pair of primers, each containing an oligo-nucleotide selected from the ADAR gene region; (ii) a second target nucleic acid obtained from amplification of the human Caspase 5 (CASP5) gene nucleic acid template with a second pair of primers, each containing an oligo-nucleotide selected from the CASP5 gene region; (iii) a third target nucleic acid obtained from amplification of the human Fibroblast Growth Factor 1 (FGFL) gene nucleic acid template with a third pair of primers, each containing an oligo-nucleotide selected from the FGF1 gene region; (iv) a fourth target nucleic acid obtained from amplification of the human Interferon Consensus Sequence Binding Protein 1 (ICSBP1) gene nucleic acid template with a fourth pair of primers, each containing an oligo-nucleotide selected from the ICSBP1 gene region; (v) a fifth target nucleic acid obtained from amplification of the human Interferon-Induced Protein 44 (IFI44) gene nucleic acid template with a fifth pair of primers, each containing an oligo-nucleotide selected from the IFI44 gene region; (vi) a sixth target nucleic acid obtained from amplification of the human Phosphoinositide-3-Kinase Catalytic Gamma Polypeptide (PIK3CG) gene nucleic acid template with a sixth pair of primers, each containing an oligo-nucleotide selected from the PIK3CG gene region; (vii) a seventh target nucleic acid obtained from amplification of the human Transporter 2 ATP-Binding Cassette Sub-Family B (TAP2) gene nucleic acid template with a seventh pair of primers, each containing an oligo-nucleotide selected from the TAP2 gene region; and (viii) an eighth target nucleic acid obtained from amplification of the human Transforming Growth Factor, Beta Receptor Associated Protein 1 (TGFBRAP1) gene nucleic acid template with a eighth pair of primers, each containing an oligo-nucleotide selected from the TGFBRAP1 gene region.

A "target nucleic acid" refers to an isolated nucleic acid that contains one or more SNPs of interest. An isolated nucleic acid refers to a nucleic acid the structure of which is not identical to that of any naturally occurring nucleic acid or to that of any fragment of a naturally occurring genomic nucleic acid. The term therefore covers, for example, (a) a nucleic acid incorporated into a vector or into the genomic DNA of a prokaryote or eukaryote in a manner such that the resulting molecule is not identical to any naturally occurring vector or genomic DNA and (b) a separate molecule such as a cDNA, a genomic fragment, a fragment produced by polymerase chain reaction (PCR), or a restriction fragment. Specifically excluded from this definition are nucleic acids present in mixtures of different (i) DNA molecules, (ii) transfected cells, or (iii) cell clones: e.g., as these occur in a DNA library such as a cDNA or genomic DNA library.

Each of the above-mentioned target nucleic acids has a nucleotide at a single nucleotide polymorphism site and is 20-1,000 (e.g., 200-1,000) nucleotides in length.

Each of the above-mentioned oligo-nucleotide is 10-50, such as 14-50 (e.g., 14-40), nucleotides in length. A primer containing such oligo-nucleotide is 10-60 (e.g., 12-55) nucleotides in length. Exemplary sequences of the target nucleic acids (SEQ ID NOs: 1-74) are listed in Table 1 below. Exemplary primers (SEQ ID NOs: 75-230), including forward ("F") and reverse ("R") primers, are listed in Table 2 below.

TABLE 1

Exemplary Target Nucleic Acids and Corresponding Primers

| Gene | SNP ID/public | SNP ID/VGV | SEQ ID NO.: | Allele | SNP Flanking Sequence | Amplification Primer ID | Amplification/ SNP Primer ID |
|---|---|---|---|---|---|---|---|
| ADAR | | VGV1473 | 1 | Y | TGGCGTGAACCCGGGAGGCGGAGCTTGCAGTG AGCCGAGATCGCGCCACTGCACTCCAGC[C/T]T | O1081-F | |

TABLE 1-continued

Exemplary Target Nucleic Acids and Corresponding Primers

| Gene | SNP ID/public | SNP ID/VGV | SEQ ID NO.: | Allele | SNP Flanking Sequence | Amplification Primer ID | Amplification/ SNP Primer ID |
|---|---|---|---|---|---|---|---|
| | | | | C/T | GAGAGACAGAGTGATACTCCATCTCTAAATCAA TCAATCAATCAATCAATCAATCAAT | O1082-R | |
| ADAR | rs903323 | VGV1600 | 2 | Y | AGCTTCAGTGGTTTTGCTCTCTGTTATGCCCTTC AGAAGCTCCTGTTTTCCTCAATCTGT[C/T]CACT GGCCTATTAGGACCTACAGTGCAGGGCCTGACC | O1077-F | |
| | | | | C/T | AGCTATCTGAGTOAGGTAAAGG | O1078R | |
| ADAR | | VGV1798 | 3 | Y | CTGAGGCAOGAGAATGGCGTGAACCCGGGAGG CGGAGCTTGCAGTGAGCCGAGATCGCGC[T/C]A CTGCACTCCAGCTTGAGAGACAGAGTGATACTC | O1081-F | |
| | | | | C/T | CATCTCTAAATCAATCAATCAATCA | O1082-R | |
| ADAR | | VGV1449 | 4 | Y | CTCTGGCTGGGAGCAGTGGCTCACGCCTGTAAT CCCAGCACTTTGGGAGGCTGAGGTGGA[T/C]CT CACGAGGTCAGGAGATTGAGACCATCCTGGCTA | O1081-F | |
| | | | | C/T | ACACGGTGAAACCCCATCTCTACT | O1082-R | |
| ADAR | | VGV1464 | 5 | Y | GGGAAGGGCCCTGCTGGGTACGTAATCAAAAG GTGCCTGATGAACCCCACCCCACCCAGA[C/T]G CAAATTTACCCACAAAGGGAGGTTCTTTGAAAT | O1081-F | |
| | | | | C/T | GGCTCCTTTCCAAAGGCTGAGGGAC | O1082-R | |
| ADAR | rsl127309 | VGV1594 | 6 | Y | GATTATTTCTGCATGGCAGTCATTGACAGTTTCT CCTTTAGGCTGAGAGAATCTCCTTT[C/T]ACAC AGCGATTCCCTAGGAAGGTGTTTAAAACAGAA | O1079-F | |
| | | | | C/T | ATAGAATAATGGAAGGAAACCGA | O1080-R | |
| CASP5 | rs518604 | | 7 | R | ATAACATTGCTCTTTGTAGGATCAAGTGGGATA TATGTAGAAGAGGGCTTGAAGTTGATC[A/G]TTT GGAAAGACAGCCAGTACTGGGATCCATAAAAC | O3101-F | |
| | | | | A/G | TTCTATTCAAAATGTTAAATGGAT | O3102-R | O3185 |
| CASP5 | rs2282658 | | 8 | S | CAAGGTGGTCTCTAACAGGATGATGACATGTTT ACTGAAAATGAGAGTTTAGAAATGAAA[C/G]TG TAGGTAGATCACAGATAACACTGCATGGGCCTT | O3107-F | |
| | | | | C/G | GGAGTTGAATATATTCTGGAAAAT | O3108-R | O3188 |
| CASP5 | rs484345 | | 9 | R | TCCAAATAATACTTACAGTCAAGTGGCTGACTC CTCCTATTTCATGGTCAACCAAATTGC[A/G]TCA TTATCATCATCAACATCACCACTATCATTGTTGT | O3157-F | |
| | | | | A/G | CATCATTATCTTTATTGAGCAA | O3158-R | O3213 |
| CASP5 | rs1699087 | | 10 | M | TGCAGGTATCTGCAGCTACCTCCTTCCTGCCAC AACCTCTGCTGATCAGAAAGGTTATTT[A/C]ATT TTGGAATTTAGTGCTCATTATATATGAGAATTG | O3159-F | O3214 |
| | | | | A/C | TACGTGATAAATAATATATAATT | O3160-R | |
| CASP5 | rs2282657 | | 11 | R | CATGGGCCTTGGAGTTGAATATATTCTGGAAAA TTTAACATATTTATCGTGTTAGATGCA[A/G]CCT TACGTTTTACACTGGTGATCTTTTGGTCCATATT | O3109-F | |
| | | | | A/G | GAGAAGTGTTTGGGTAAACATT | O3110-R | O3189 |
| CASP5 | rs3181318 | | 12 | R | TGGTCATCCATTGTATTCAGATTTCTCTCTCTTG CTCAAACTCATGATGACCTACCTGAA[A/G]TGTG TGCACCCAGGACAGTCCATTCTCTTGTCTAGAC | O3113-F | O3191 |
| | | | | A/G | TGTAAATTATTCCTACTAGACT | O3114-R | O3805 |
| CASP5 | rs1790203 | | 13 | R | GGGGTCTAAATGAAAAACTTTGGGAGAAGAGC AACGTGCTCTGCACTGACCAGAAGAAAG[A/G]C ATTACTTCAGTATTTTCTGTATATGGCTTGATTA | O3129-F | O3807 |
| | | | | A/G | TCCCTTATCCAAAATGCATGCTAC | O3130-R | O3199 |
| FGF1 | rs249926 | VGV567 | 14 | Y | GTTTCGCCCTFGTGAGGCACACTGGGCAATGCT GCCATTCCCATTCCACAGGTGAGGAAA[C/T]TG AGTCTCAGCGAGACTAAATGATTTTCCTGAAAA | O843-F | |
| | | | | C/T | TTATCTGGGAACACTAGAGACACT | O844-R | |
| FGFI | | VGV679 | 15 | M | GAACCCTAGTAAATAGAAGTTTCGCCCTTGTGA GGCACACTGGGCAATGCTGCCATTCCC[A/C]TTC | O843-F | |

TABLE 1-continued

Exemplary Target Nucleic Acids and Corresponding Primers

| Gene | SNP ID/public | SNP ID/VGV | SEQ ID NO.: | Allele | SNP Flanking Sequence | Amplification Primer ID | Amplification/ SNP Primer ID |
|---|---|---|---|---|---|---|---|
|  |  |  |  | A/C | CACAGGTGAGGAAACTGAGTCTCAGCGAGACT AAATGATTTTCCTGAAAATTATCT | O844-R |  |
| FGFI | rs2282799 | VGV714 | 16 | M | GGGGGGCTTGAAGCTTCTTTCGCAGAGTTTGCA AACAGAAAGAATGCATAATGGCAAGAA[A/C]GT TAATTGTCCAGGGCTGCTCCAGGTAGAAAGGGG | O843-F |  |
|  |  |  |  | A/C | CAGAGTAGGCTTGAACTCGAGCCT | O844-R |  |
| FGFI | rs2282798 |  | 17 | R | CAGGTGAGGAAACTGAGTCTCAGCGAGACTAA ATGATTTTCCTGAAAATTATCTGGGAAC[A/G]CT AGAGACACTTCAATTTCTAGTCAGGAAAGGACT | O843F |  |
|  |  |  |  | A/G | GGAAGCGTCCCAGGGCTGGGGGC | O844-R |  |
| FGF1 |  | VGV676 | 18 | Y | GAGGCAATTCTGTTTGAATAACCCTTGAAAC TCAGAAGGGCTCTGGCAGTACCACCAC[C/T]GG GCAGAAGAGGGCAACAGAACCACATTCAGGGA | O843-F |  |
|  |  |  |  | C/T | GTACATCCGTGCCCAGGACTCCTCT | O844-R |  |
| FGF1 |  | VGV573 | 19 | M | TCACATTTAGTCAGGGAGCATCCGTCTCATGCC TGGCCGAGGCAATTCTGTTTCTGAATA[A/C]CCC TTGAAACTCAGAAGGGCTCTGGCAGTACCACCA | O843-F |  |
|  |  |  |  | A/C | CTGGGCAGAAGAGGGCAACAGAA | O844-R |  |
| FGF1 |  | VGV700 | 20 | Y | CAAGGAATCAAAATATCTCCTTGCCAGGCCGT GTGGATCACATTTAGTCAGGGAGCATC[C/T]GTC TCATGCCTGGCCGAGGCAATTCTGTTTCTGAAT | O843-F |  |
|  |  |  |  | C/T | AACCCTTGAAACTCAGAAGGGCT | O844-R |  |
| FGF1 | rs2282797 | VGV674 | 21 | Y | TTTCGATTGGCTTTTAGAAACGCTCTTTCTGAAG GAAGTCTTAACGTGTGACTCTGTCAC[C/T]TCAG TCTCTAATTATGCTCAAACTAGTGATCAAGGAA | O843-F |  |
|  |  |  |  | C/T | TCAAAAATATCTCCTTGCCAGG | O844-R |  |
| FGF1 |  | VGV625 | 22 | S | TTTTCGATTGGCTTTTAGAAACGCTCTTTCTGAA GGAAGTCTTAACGTGTGACTCTGTCA[C/G]TTCA GTCTCTAATTATGCTCAAACTAGTGATCAAGGA | O843-F |  |
|  |  |  |  | C/G | ATCAAAAATATCTCCTTGCCAG | O844-R |  |
| ICSBP1 | rs385989 |  | 23 | K | TGACGACATGTGCCCAAGGTGGTCGGGGCACA GCCTGGTTTTATACATTTTAGGGAGACA[G/T]GA GACATCAATCAATACATGTAAGAAGTACACTGG | O2740-F | O2789 |
|  |  |  |  | C/G | TTCCATCCAGAAAGACGGGGACAG | O2741-R |  |
| ICSBP1 | rs305067 |  | 24 | S | AGTGATTGGCTCAGGAAGGGGCATGGGACTGA ATAATGGCCAATGAGCTGAGAGGAAAAA[C/G]A CCTGCTGGGGCTTCCAGGAAGGTCCCTCCTTCC | O2744-F |  |
|  |  |  |  | C/G | TTGCCACCTGGTGTGTCCAGAGGAT | O2745-R | O2791 |
| ICSBP1 | rs305097 | VGV1824 | 25 | R | CACCAAGAGAACATGTTCTAGGAGGCAGGAAG AAGCAGCTCGCAGATTCTTAAGTCTCAC[A/G]CC TAGAAACGGACACAGCATCACTTCTACCTATGC | O2750-F |  |
|  |  |  |  | A/G | TGCTGGTCAAAGCAGGCACAGAGC | O2751-R | O2794 |
| ICSBP1 |  | VGV1826 | 26 | M | GATTCTTAAGTCTCACGCCTAGAAACGGACACA GCATCACTTCTACCTATGCTGCTGGTC[A/C]AAG CAGGCACAGAGCCCACTGGATTGAAGAAAGAG | O2750-F |  |
|  |  |  |  | A/C | GCATAGACCCCCACCTTTAAAGGG | O2751-R |  |
| ICSBP1 | rs305088 |  | 27 | Y | CGTGCGAGGTGCTGCGCTCACAGTATTACTCAT GCACCTTTCTGATAAGAAAAGTGAAAA[C/T]GT GAAGTTGAAAACTGAAGACGCCCAGCAACTTC | O2754-F |  |
|  |  |  |  | C/T | CTGAATCCAGCCCTCCACGTCCTGC | O2755-R | O2796 |
| ICSBPI | rs870614 | VGV1827 | 28 | R | ACTGGGAACCTCCATAGTTACCACATGCTGCGC TGACTTCTCTAACACGCTTTGGCCAAT[A/G]ATG TTTCCCTAATCACAGCAGCTCCTCATTTAGAAT | O2756-F |  |
|  |  |  |  | A/G | GTGTTCTTATTTAGGATGCGTTC | O2757-R | O2797 |
| ICSBP1 | rs305061 |  | 29 | Y | ATGAAAGTGCTGTTCTCATCACTTCCTATCCAT GGTCCATGCTGTCCGTGTGACTTACCA[C/T]GGT | O2748-F | O2793 |

TABLE 1-continued

Exemplary Target Nucleic Acids and Corresponding Primers

| Gene | SNP ID/public | SNP ID/VGV | SEQ ID NO.: | Allele | SNP Flanking Sequence | Amplification Primer ID | Amplification/ SNP Primer ID |
|---|---|---|---|---|---|---|---|
| | | | | C/T | GGACGTTGACCTTGGCCACCTGGCTGGCTGTTG GGTTCTCCACTGGAAGTTTACTC | O2749-R | |
| ICSBP1 | rs305095 | | 30 | Y | ACCTATGCTGCTGGTCAAAGCAGGCACAGAGC CCACTGGATTGAAGAAAGAGGCATAGAC[C/T]C CCACCTTTAAAGGGCTGAGTGTCAGAGAACTTG | O2752-F | O2795 |
| | | | | C/T | TGGCCAACATTAATCCACCACAACT | O2753-R | |
| IFI44 | rs2148686 | VGV199 | 31 | K | AAGCCCTCAAATCCCATTCCTAATCTGATGAGT CTATGGACCAATTTGTGGAGGACAGTA[G/T]ATT AAATAGATCTGATTTTTGCCATCAATGTAAGGA | O857-F | |
| | | | | G/T | GGATAAAAACTTGCATACCAATT | O858-R | |
| IFI44 | rs2070123 | VGV2188 | 32 | Y | GGAAAATATATATGATTTGCCACTAGATCAAGA AGTATGGCAGTGACAACTCGTTTGACA[C/T]GGT TGCACGAAAAGATCCTGCAAAATCATTTITGAG | O4631-F | O4650 |
| | | | | C/T | GGAAGCGGCTTAGCCTTCTCTAT | O4632-R | O7081 |
| IFI44 | rs273249 | VGV2191 | 33 | R | CCTCAGTATAAAAGCTCTATCAGTACCATGAAC AATCTCATCATAATCACACTTAATATC[A/G]TTT CATATAATCACAATCAAAACTGGAAACAATTAA | O4637-F | |
| | | | | A/G | AACATTTTAGCATATTTTTATAG | O4638-R | O4653 |
| IFI44 | | VGV33 | 34 | R | AGGTGGTTTCATTTGAGGCCTCATTTGTTACCAT TGAAATCAATGAAGGTGACTCCCCAT[G/A]TCA GAGAAATTCCAGATACTAATAAGTAGTCCAGG | O861-F | |
| | | | | A/G | GGAGTTTTTTGGGGAGATGAGGGT | O862-R | |
| IFI44 | | VGV2189 | 35 | S | CTGTCTGCCTTGAGAACTTATGAACCATATGGA TCCCTGGTTCAACAAATACGAATTCTG[C/T]TGC TGGGTCCAATTGGAGCTGGGAAGTCCAGCTTTT | O4635-F | |
| | | | | C/G | TCAACTCAGTGAGGTCTGTTTTC | O4636-R | |
| IFI44 | | VGV205 | 36 | Y | GGTCCAATTGGAGCTGGGAAGTCCAGCTTTTC AACTCAGTGAGGTCTGTTTTCCAAGGG[C/T]ATG TAACGCATCAGGCTTTGGTGGGCACTAATACAA | O859-F | |
| | | | | C/T | CTGGGATATCTGAGAAGGTAAGC | O860-R | |
| IFI44 | | VGV2187 | 37 | M | GGGGTGTACAAATTATTGTATTTTAAAGTCAAT CAGAATAGTTTATTCTTGTATTATAAC[C/A]ATA ACAGTTCACTAATTAAATTAAATTTAGGAATTG | O4637-F | |
| | | | | A/C | AATTGTTAAGTTAATTTGGTTTT | O4638-R | |
| IFI44 | rs2296718 | VGV96 | 38 | K | CATAAATTTTAGTTACCTCTTCCAAGAGGTGGT TTCATTTGAGGCCTCATTTGTTACCAT[G/T]GAA ATCAATGAAGGTGACTCCCCATGTCAGAGAAAT | O861-F | |
| | | | | G/T | TCCAGATACTAATAAGTAGTCCA | O862-R | |
| IFI44 | rs2296717 | VGV225 | 39 | Y | TCCAAGAGGTGGTTTCATTTGAGGCCTCATTTG TTACCATTGAAATCAATGAAGGTGACT[C/T]CCC ATGTCAGAGAAATTCCAGATACTAATAAGTAGT | O861-F | |
| | | | | C/T | CCAGGGGAGTTTTTTGGGGAGAT | O862-R | |
| IFI44 | rs1051047 | | 40 | R | ACATTGTAGTACTTGTAAATAACTAGAAATAAC ATGATTTAGTCATAATTGTGAAAAATA[A/G]TA ATAATTTTTCTTGGATTTATGTTCTGTATCTGTG | O4647-F | |
| | | | | A/G | AAAAAATAAATTTCTTATAAAAC | O4648-R | |
| PIK3CG | rs1526083 | | 41 | R | TGTTATCAATGGAAGCCTTCTCAAAAGGAATTG ATTTGCATATGCACAGGCACTCCATTC[A/G]GTT GTCATCAAATGCCCTTTGTTCAGAGCTTCATCAT | O2378-F | |
| | | | | A/G | CGGCAAAAGTAGATATGATGAA | O2379-R | O2426 |
| PIK3CG | rs3779501/IMS-JST135578 | | 42 | Y | TGCTGCTTTTAAAATTATGAACTATTTCAAACTT ACAGAAAAGCACAGAGAACAATGAAA[C/T]ACC TATGCACTCACAAGATTAATTGTGTTTTTTACA | O2382-F | O2428 |
| | | | | C/G | TTTTATCAGTTCTTCCTCATCA | O2383-R | |
| PIK3CG | rs2037718 | | 43 | S | GATCCTATTTACAGCATTCTATTTATTAATTTTT ATAAAAACCTAGTTTATTAAAAACTA[C/G]TTAC | O2396-F | |

TABLE 1-continued

Exemplary Target Nucleic Acids and Corresponding Primers

| Gene | SNP ID/public | SNP ID/VGV | SEQ ID NO.: | Allele | SNP Flanking Sequence | Amplification Primer ID | Amplification/ SNP Primer ID |
|---|---|---|---|---|---|---|---|
| | | | | C/G | AGTAATATTTGATTTTTTAAAGACAATTAGGTC ATTTGTAAATAATAAGTTTTCC | 02397-R | 02435 |
| PIK3CG | rs3173908 | | 44 | Y | GCTAGGATTATTTGCAGGTTTGGTTTTTTCTCAT TTGTCTGTGGCATTGGAGAATATTCT[C/T]GGTT TAAACAGACTAATGACTTCCTTATTGTCCCTGA | 02400-F | 02437 |
| | | | | C/T | TATTTTGACTATCTTACTATTG | 02401-R | 03264 |
| TAP2 | rs1871665 | | 45 | Y | GGAAAAGAGTAATGATTCTGGAAAGAAAGGTG ATAAGCCTCAGAGTAAGATCTTCAGGGA[C/T]T AGCAAGATGAGCTGGGAAAGAAGAGTGAGAGG | 02882-F | 02821 |
| | | | | C/T | GAGAAGCATACCCATCCTGAGAGAGT | 02883-R | |
| TAP2 | rs2071543 | | 46 | K | CCTCCACTCCTCAGCGCCCGCCTCCCTGCATCC CTAGGGGCTTCCCTACTGCCCCGACCT[G/T]CAT TCCCCGGGTAAAGCGAGCTCTGGAGATCGCAT | 02888-F | 02824 |
| | | | | G/T | AGAGAAACTGTAGTGTCCTGGGT | 02889-R | |
| TAP2 | rs1800453 | | 47 | Y | AATGCTCGGGCAACGCCACTGCCTGTCGCTGA CCCCCTGACAGCTGGCTCCCAGCCTCG[C/T]CTA CCTCTGCAGAGCAAAGGGCCAAGATGAGAACG | 02892-F | 02826 |
| | | | | C/T | GTATAGCCACATGTGTGCACGCAT | 02893-R | |
| TAP2 | rs1894407 | | 48 | M | AACTGTGAGAAATAAATTTCTGTTCTTCATAAA TTACCCTATCTCGTGTATCTTGTTACA[A/C]TAA CACAAATGGACTAAGACAGAGAGCATAAGGCT | 02866-F | 02813 |
| | | | | A/C | TGGGGGAAGAAGGGTACACTTCTT | 02867-R | |
| TAP2 | rs2857101 | | 49 | Y | TCAGATCATCTTCTTCTGTGAGGGCTGCAGCTT CCATGTAGTTGGGAGATACAGGAATTA[C/T]TAT TCCTGTTTTATGAATAAAGGACATTTGTGGGAG | 02872-F | 02816 |
| | | | | C/T | AGAAAGGAATCAGGCCAGAGTTC | 02873-R | |
| TAP2 | rs183585 | | 50 | R | CCTGATTTAAGCAAAGTATAATAAACACACTCA TACACATATACTACATGGATACCACAA[A/G]TG GAAATTTGACAATTGACTATTTGATAAATTTTA | 02876-F | 02818 |
| | | | | A/G | AGAACTACTGTTAATTTTTTGGTG | 02877-R | |
| TAP2 | rs991760 | | 51 | R | TCATAGTCAATTACTCTGTGTTGGGTCTACACC ACATCTGCACATACTATGAGCCCTTCC[A/G]TTG GAGATAATTTTCACTTGCGGAGCTGCTTCACTT | 02900-F | |
| | | | | A/G | CTACCTGTAGGAGCCTCATCTCC | 02901-R | 02830 |
| TAP2 | rs1383269 | | 52 | R | ATTGGCTCATACTACTGTGGGAGCTGGCACGGT CGAAATCTGCAGGTAGGCTGGAGACCC[A/G]GG AAGAGCTGATGTTGCGGCTTGAGTCTGAAGGTG | 02910-F | 02835 |
| | | | | A/G | GTCCAGAGGCGAGAATTCCCTCTTC | 02911-R | |
| TGFBRAP1 | rs2241796 | VGV2200 | 53 | Y | GTGAAGTGACAACAGCTTCAGCTCGTCATCGAT GTTATACAGAAACACAAAAGGAATCCC[C/T]GG CCTGTGATGAAGGAGAGGCCGTTGCTGTGTGTT | 04719-F | 04781 |
| | | | | C/T | CAGGACACCTCAGAGCAGGCACAT | 04720-R | 07086 |
| TGFBRAP1 | | VGV2192 | 54 | R | CAGAAACACAAAAGGAATCCCCGGCCTGTGAT GAAGGAGAGGCCGTTGCTGTGTGTTCAG[G/A]A CACCTCAGAGCAGGCACATAAAGTGCTGGAGG | 04719-F | |
| | | | | A/G | GTGACACAGCCTGTCTGGATGTCCTC | 04720-R | |
| TGFBRAP1 | rs1866040 | VGV2204 | 55 | R | GGAGGGTGTGCCATCCAGGAGGCGACACCCCC ATCCAGCACACGGGCCCTTCCACCCGCT[A/G]TC GGTCCTGCTAAAGGTACGAGGCTAAAACCGGC | 04719-F | |
| | | | | A/G | CTCTCCAGAAAAGAACGCTCAGTGT | 04720-R | |
| TGFBRAP1 | | VGV2197 | 56 | Y | AAAACTGTCATGATGACAAAATGCAAGCATGA CGTAAAATGCCTAGGTCAGTGCCTGGCA[C/T]A CAGCACATGCTGGGTAAGCGCCTGATATTCTGA | 04723-F | 07088 |
| | | | | C/T | TGCTGCTCTCCTCCCTACAGACTCT | 04724-R | 04783 |
| TGFBRAP1 | rs2576737 | VGV2325 | 57 | Y | CTTCCCTCTAGCCAACAGGTGCTTTTTCACTGCC AGCATTTCTCAGCCTCCAGGACAGGC[C/T]GAGT | 04729-F | 04786 |

TABLE 1-continued

Exemplary Target Nucleic Acids and Corresponding Primers

| Gene | SNP ID/public | SNP ID/VGV | SEQ ID NO.: | Allele | SNP Flanking Sequence | Amplification Primer ID | Amplification/ SNP Primer ID |
|---|---|---|---|---|---|---|---|
| | | | | C/T | CTTGCTCATGGCTCCCCTCCCTCCTCCAGGCCCA CAAGCTCCATGTTGGCAGTGG | 04730-R | 07089 |
| TGFBRAP1 | rs1866039 | | 58 | Y | CGTTGCTGTGTGTTCAGGACACCTCAGAGCAGG CACATAAAGTGCTGGAGGGTGACACAG[C/T]CT GTCTGGATGTCCTCGGGAGGGTGTGCCATCCAG | 04721-F | 04782 |
| | | | | C/T | GAGGCGACACCCCCATCCAGCACA | 04722-R | 07087 |
| TGFBRAP1 | | VGV2196 | 59 | M | AATGTGGGGTTCTCAACTGGCCTGGGAGGCAGC TCTGGGCACGCCCATTTCCTGAGCATG[A/C]GAC TGCTCTCTGCCTCAATTTCCTCTCCTGTGAAATG | 04723-F | |
| | | | | A/C | GAGATGCTGACAGTAAATACTG | 04724-R | |
| TGFBRAP1 | | VGV2203 | 60 | Y | CGTAAAATGCCTAGGTCAGTGCCTGGCACACAG CACATGCTGGGTAAGCGCCTGATATTC[T/C]GAT GCTGCTCTCCTCCCTACAGACTCTCTTAATCACC | 04723-F | |
| | | | | C/T | AGCGTCCAAAAGGGGAGAAAAA | 04724-R | |
| TGFBRAP1 | hCV2099139 | | 61 | R | GACAATACTGAGATCATCCTCACCGAGAAGAA AGTGGACTCGGTATAAATCAGATTTCTG[A/G]A GCAGCCGCCGCAGCTTGGCCTGCGTCTCGGTGG | 04727-F | 04785 |
| | | | | A/G | CCTCTGCACCCTTGCCACTGGCGGA | 04728-R | |
| TGFBRAP1 | rs2576738 | | 62 | M | AGGGCCCAGTGTGGCCCAGGTCTGGGTGCTTCC TCCTCCCAAAGATCAAGTCCTTCAGG[A/C]AA CCACCTAATCCTGCTCCAGAAAACAGCAGTGTC | 04731-F | |
| | | | | A/C | AGACTTCTGAGGGGTCGAGGAGCG | 04732-R | 04787 |
| TGFBRAP1 | rs2241800 | VGV326 | 63 | Y | TGAAGAGAATACCCAGCTGAGCCTGGAAACCA AGGCAGAAAAGCAACACCCAGGATAACA[C/T]G CCATCAGAGTCTGCGCAAAGGCACCATCACAGC | O619-F | |
| | | | | C/T | TCTGCTGAAACCAGCATTTTCCTGG | O620-R | |
| TGFBRAP1 | rs1020063 | VGV308 | 64 | Y | AAAGCAACACCCAGGATAACACGCCATCAGAG TCTGCGCAAAGGCACCATCACAGCTCTG[C/T]TG AAACCAGCATTTTCCTGGCACTAAATTACAAAC | O619-F | |
| | | | | C/T | AGATTTGTTGAATGGTCCTTGAAG | O620-R | |
| TGFBRAP1 | rs1020064 | VGV296 | 65 | Y | AGAAATATTCATGTGGCCATTTCTGTGGGGACT CTCGTAGAATTTCAGAGCCTAACATTG[G/T]AAT GCAACAAACAGTTCCTTTCCCATCTCCTCTCCG | O619-F | |
| | | | | C/T | GAACCTCCTTGTCCTGGCTACAA | O620-R | |
| TGFBRAP1 | rs2576741 | VGV419 | 66 | V | GAATGGCGAGGAAGGACCCAGGATCCATGCTG CCTGCGATGTTCAGAGCATCCTCCTTCA[C/T]CC AAGCTCTGATCAGCTGTCCTCCTCTACTGGCTTC | O619-F | |
| | | | | C/T | CACCTCTGGCTGCCCTTCCTTCC | O620-R | |
| TGFBRAP1 | rs2576743 | | 67 | Y | CACCCAGGCTTTCTTAGTCAGAGATGCAGAAAT GCTGCATGTTCCATCTCCTGCTGGTGA[C/T]GTC CAACCCACATGAACACACCAACATCCGACACTC | 04741-F | 04792 |
| | | | | C/T | CTGCAATAAAGGGGCCAGTTTAT | 04742-R | 07090 |
| TGFBRAP1 | rs3792047/IMS-JST149411 | | 68 | Y | TCTCTGATCCCACGCCCCACTCCGTCACCGTCC AGCATGGCTGGTGTCCTCGTCTTGCCA[C/T]TGT CTATATGAAATGGCTCCTGGACATGTTTCTTCA | 04743-F | 04793 |
| | | | | C/T | CTCTGTTCCTACAGATGCCAACA | 04744-R | 07091 |
| TGFBRAP1 | rs920217 | | 69 | Y | CAGCTATAGTAAGAATTTTTTGAGAAAGATGAC AACCACAACCAAATGAGTCTGCAAATA[C/T]CA CAGCAGGACACACACCATGTAAACCCTGGAGC | 04747-F | 04795 |
| | | | | C/T | TGAGGGAAGATGAACAGGCACACGG | 04748-R | 07093 |
| TGFBRAP1 | rs2576750 | | 70 | W | AGAGTAGCTGAATTATTTACCTTCTTCAAGAAG CACTGTCATAGGACAGGGTTTAAGACT[A/T]TA AACCTCTGGTTTAAAGTCTGGTGGTTACTATGC | 04757-F | 04800 |
| | | | | A/T | TGAAGATAGAATCTGTATATAGGT | 04758-R | 07094 |
| TGFBRAP1 | | VGV2199 | 71 | W | GAATTTAACAACGTAATAATCCCTAAAGGAAA ACACACTGCCTCCTTCTCATCTGTCGCT[A/T]GT | 04771-F | |

TABLE 1-continued

Exemplary Target Nucleic Acids and Corresponding Primers

| Gene | SNP ID/public | SNP ID/VGV | SEQ ID NO.: | Allele | SNP Flanking Sequence | Amplification Primer ID | Amplification/ SNP Primer ID |
|---|---|---|---|---|---|---|---|
| | | | | A/T | CCATATGAAAAGTAGCAACGTCTGGTGGACAA GGGCAGCCTCAGAATGGGCTCTGGG | 04772-R | |
| TGFBRAP1 | rs1561237 | | 72 | R | CAGATTCCCACACACTGGACTTCCTCTGACTGG CTGATGGCAGGGATCCTGGCTTTAGGC[A/G]TG AGTATCTTTCTTTCTTTGCATCTTCCTACAATTT | 04771-F | |
| | | | | A/G | ACAGTTTTTGTATAAATACAATG | 04772-R | 04807 |
| TGFBRAP1 | hCV2099090 | | 73 | W | CTCAAGGTTACCTGGCTACAAGGTGATGAAACA GGGCTTTGACCCTAGTTTTTGTTCGTG[A/T]CTC CAAGGCCATATTCTTATTGATTGAGGGGAACAA | 04775-F | 04809 |
| | | | | A/T | GTATGATTTCAGATCCTCTCCTA | 04776-R | 07095 |
| TGFBRAP1 | rs2246094 | | 74 | S | CCCCTACCCTAGTGTGACTCATGGCCACATAAA TGCCCCATCCCCAGTGGTGCTTCAGCT[C/G]TGA CCCAGTGGAACCAGTGTCACCGGCTCAGCCTCC | 04779-F | 04811 |
| | | | | C/G | AGGTAGGGGACTGGCTTCCCAGG | 04780-R | |

Notes:
1. SNPID/public: SNP ID in public database dbSNP in the Entrez system of the National Center for Biotechnology Information at http://www.ncbi.nlm.nih.gov/SNP/index.html (started with "rs (reference SNP)") and in the SNP database of Celera Genomics (started with "hCV").
2. SNPID/VGV: SNP ID in the database of Vita Genomics, Taipei, Taiwan.
3. Amplification Primer: a primer that can be used in PCR amplification (same for Table 2 below).
4. Amplification/SNP Primer: a primer that can be used in PCR amplification and in single-base-extension-based SNP typing (same for Table 2 below).
5. Each SNP is bracketed.

TABLE 2

Amplification Primers and corresponding Amplification/SNP Primers

| Amplification Primer ID | SEQ ID NO.: | Primer Sequences | Amplification SNP/Primer ID | SEQ ID NO.: | Primer Sequences |
|---|---|---|---|---|---|
| 01081-F | 75 | GAGGTGAAAATGGGAACAAAGG | | | |
| 01082-R | 76 | AAAACTACAACCAAGCCTGTCC | | | |
| 01077-F | 77 | TAAGCCGTTTTCTGAGAGAGGTG | | | |
| 01078-R | 78 | CTCTTTGCTCAGTCTGGGATTT | | | |
| 01079-F | 79 | GGAGAGAATATGGGAGTCTAGGA | | | |
| 01080-R | 80 | GCATAGTTAGCCTTTTGGGTCTC | | | |
| 03101-F | 81 | TTCACATTTTTATCTGGACACTT | | | |
| 03102-R | 82 | ACACTTTACAGTCAAAGGCATAC | 03185 | 177 | CCAGTACTGGCTGTCTTTCCAAA |
| 03107-F | 83 | CATGTTTACTGAAAATGAGAGTTT | | | |
| 03108-R | 84 | ATGATACCAAAATTGAAGACAAG | 03188 | 178 | GCAGTGTTATCTGTGATCTACCTACA |
| 03157-F | 85 | GACTCCTCCTATTTCATGGTC | | | |
| 03158-R | 86 | GCCCCATACTTGATATTAGATGT | 03213 | 179 | GTGGTGATGTTGATGATGATAATGA |
| 03159-F | 87 | GAGAATCCAAATGCAGATAGAG | 03214 | 180 | CCTCTGCTGATCAGAAAGGTTATT |
| 03160-R | 88 | ATGTTTTTCAGGGATAGACAAA | | | |
| 03109-F | 89 | CATGTTTACTGAAAATGAGAGTTT | | | |

TABLE 2-continued

Amplification Primers and corresponding Amplification/SNP Primers

| Amplification Primer ID | SEQ ID NO.: | Primer Sequences | Amplification SNP/Primer ID | SEQ ID NO.: | Primer Sequences |
|---|---|---|---|---|---|
| O3110-R | 90 | ATGATACCAAAATTGAAGACAAG | O3189 | 181 | AAAAGATCACCAGTGTAAAACGTAAGG |
| O3113-F | 91 | TCCATTGTATTCAGATTTCTCTC | O3191 | 182 | CTCAAACTCATGATGACCTACCTGAA |
| O3114-R | 92 | TAAGCACTTTTAAGCATTTGAG | O3805 | 183 | CTGTCCTGGGTGCACACA |
| O3129-F | 93 | AAGGGGTCTAAATGAAAAACTT | O3807 | 184 | GCTCTGCACTGACCAGAAGAAAG |
| O3130-R | 94 | CACATGATATTCAAAGGAAATGT | O3199 | 185 | TCAAGCCATATACAGAAAATACTGAAGTAATG |
| O843-F | 95 | AAGAACAAGGACCAAGAGGACAG | | | |
| O844-R | 96 | CTTGTAGAGCTCAAAGGCATACG | | | |
| O2740-F | 97 | AGGTTTATTCGACAAAGTTAAGG | O2789 | 186 | GCCTGGTTTTATACATTTTAGGGAGACA |
| O2741-R | 98 | GGTTGTCTCTAAACTCAAAGAA | | | |
| O2744-F | 99 | ACTGAATAATGGCCAATGAG | | | |
| O2745-R | 100 | AGGTTCCTTGACTCCAACTC | O2791 | 187 | TGGAAGCCCCAGCAGGT |
| O2750-F | 101 | AGCAGCATAAATGGACTTCTT | | | |
| O2751-R | 102 | CAGTTGTGGTGGATTAATGTT | O2794 | 188 | TGATGCTGTGTCCGTTTCTAGG |
| O2754-F | 103 | TCCACACCTCAAGGTAGTTC | | | |
| O2755-R | 104 | GTGAGGTGAGATCCTGAAAC | O2796 | 189 | GGCGTCTTCAGTTTTCAACTTCAC |
| O2756-F | 105 | GACTGGGAACCTCCATAGTTA | | | |
| O2757-R | 106 | GTATCCTACGGGACAGAGTTTAT | O2797 | 190 | AGCTGCTGTGATTAGGGAAACAT |
| O2748-F | 107 | GCTTTTCTGATGTTTTTCTCAT | O2793 | 191 | GCTGTCCGTGTGACTTACCA |
| O2749-R | 108 | TCTTTAATGGATTTAGTGAGTCTG | | | |
| O2752-F | 109 | GGACACAGCATTACTTCTACCTA | O2795 | 192 | ACTGGATTGAAGAAAGAGGCATAGAC |
| O2753-R | 110 | ACTCCACAGAAAAGATCAATGT | | | |
| O857-F | 111 | ATGCTAAGGTACCCACAAGATGG | | | |
| O858-R | 112 | CTTCTTGGCCATGGGAATTTG | | | |
| O4631-F | 113 | TTTGCCACTAGATCAAGAAGTAT | O4650 | 193 | GGCAGTGACAACTCGTTTGACA |
| O4632-R | 114 | CATACTTTCCTTCCTGGTAACTC | O7081 | 194 | GCAGGATCTTTTCGTGCAACC |
| O4637-F | 115 | ATCAGTACCATGAACAATCTCAT | | | |
| O4638-R | 116 | AAACCAAATTAACTTAACAATTCAA | O4653 | 195 | AATTGTTTCCAGTTTTGATTGTGATTATATGAAA |
| O861-F | 117 | TAGAGCCCTTTGGTCTTTAGTC | | | |
| O862-R | 118 | CTGGGCAACAGAAACTTCATC | | | |
| O4635-F | 119 | CCTAACCTCAGTCAATTGTTAAA | | | |
| O4636-R | 120 | AAATGTGCTTACCTTCTCAGATA | | | |
| O859-F | 121 | AAACAGGCTCAGGAAGAGCTTA | | | |
| O860-R | 122 | CTGCCTTCAGACTTCCTCTTACA | | | |
| O4647-F | 123 | AGTATCTAAGACCAAAGGGATGT | | | |

TABLE 2-continued

Amplification Primers and corresponding Amplification/SNP Primers

| Amplification Primer ID | SEQ ID NO.: | Primer Sequences | Amplification SNP/Primer ID | SEQ ID NO.: | Primer Sequences |
|---|---|---|---|---|---|
| 04648-R | 124 | AAAGCAGTGAATATCAGAAGATG | | | |
| 02378-F | 125 | GCATTACCTTCTACAATTGGTC | | | |
| 02379-R | 126 | GTGAAGTACTAATGTCTGCAAAAC | 02426 | 196 | GAACAAAGGGCATTTGATGACAAC |
| 02382-F | 127 | AAAGGATACACCATTTCTATTCA | 02428 | 197 | ACAGAAAAGCACAGAGAACAATGAAA |
| 02383-R | 128 | TGAGGAAGAACTGATAAAATGTAA | | | |
| 02396-F | 129 | GCATAGGTTCTACATGTTTTATGT | | | |
| 02397-R | 130 | AATCAGAAAAGTGAAGGAAAACT | 02435 | 198 | ATGACCTAATTGTCTTTAAAAAATCAAATATTACTGTAA |
| 02400-F | 131 | CTCTTTTCCTACCTGAACTCTTC | 02437 | 199 | TGTCTGTGGCATTGGAGAATATTCT |
| 02401-R | 132 | TAAACCCAGATGAAAATAGATGT | 03264 | 200 | ACAATAAGGAAGTCATTAGTCTGTTTAAACC |
| 02882-F | 133 | AGTGAAGGGAAAAGAGTAATGAT | 02821 | 201 | GCCTCAGAGTAAGATCTTCAGGGA |
| 02883-R | 134 | TTAAGTCTCAGATGGAATGTCTC | | | |
| 02888-F | 135 | CTAACTTGCACTTCCTCCTCT | 02824 | 202 | CCCTACTGCCCCGACCT |
| 02889-R | 136 | AGGACACTACAGTTTCTCTATGC | | | |
| 02892-F | 137 | CATCATCCAGGATAAGTACACAC | 02826 | 203 | CTGGCTCCCAGCCTCG |
| 02893-R | 138 | TTCTGTTCATCTTCCCAGAAT | | | |
| 02866-F | 139 | GGTATCATGGTAACCACAAGTT | 02813 | 204 | AATTACCCTATCTCGTGTATCTTGTTACA |
| 02867-R | 140 | AATCGTCCTGTCTTTATTCTTTT | | | |
| 02872-F | 141 | TAGGTTTGACTGTTGCATTATTT | 02816 | 205 | CATGTAGTTGGGAGATACAGGAATTA |
| 02873-R | 142 | AATTTCACAGAGGGTAAAATAGG | | | |
| 02876-F | 143 | TATTCTGAAGCAAATCCAAGATA | 02818 | 206 | TCTTAAAATTTATCAAATAGTCAATTGTCAAATTTCCA |
| 02877-R | 144 | AGTCACAATATGTGGACCATTT | | | |
| 02900-F | 145 | CAATTACTCTGTGTTGGGTCTAC | | | |
| 02901-R | 146 | TCATCTTTCCACTTTCTCTATTG | 02830 | 207 | CTCCGCAAGTGAAAATTATCTCCAA |
| 02910-F | 147 | ATAGATTTTGGGTAAAGCAGATT | 02835 | 208 | GCCGCAACATCAGCTCTTCC |
| 02911-R | 148 | TTGGCAGAGAGAGATTTATTTTA | | | |
| 04719-F | 149 | TCGATGTTATACAGAAACACAAA | 04781 | 209 | TGTTATACAGAAACACAAAAGGAATCCC |
| 04720-R | 150 | ACACACTGAGCGTTCTTTTC | 07086 | 210 | CCTCTCCTTCATCACAGGCC |
| 04723-F | 151 | AGAATGTGGGGTTCTCAACT | 07088 | 211 | CGACTGCTCTCTGCCTCAATTTC |
| 04724-R | 152 | ATTAAGAGAGTCTGTAGGGAGGA | 04783 | 212 | CAGCATCTCCATTTCACAGGAGA |
| 04729-F | 153 | ATACTGTCCTGAGCCTGCTA | 04786 | 213 | CAGCCTCCAGGACAGGC |
| 04730-R | 154 | AAGTCTGACACTGCTGTTTTCT | 07089 | 214 | GGGAGCCATGAGCAAGACTC |
| 04721-F | 155 | TCGATGTTATACAGAAACACAAA | 04782 | 215 | GTGCTGGAGGGTGACACAG |
| 04722-R | 156 | ACACACTGAGCGTTCTTTTC | 07087 | 216 | CCCGAGGACATCCAGACAG |

TABLE 2-continued

Amplification Primers and corresponding Amplification/SNP Primers

| Amplification Primer ID | SEQ ID NO.: | Primer Sequences | Amplification SNP/Primer ID | SEQ ID NO.: | Primer Sequences |
|---|---|---|---|---|---|
| 04727-F | 157 | AAGGGAGACAATACTGAGATCAT | 04785 | 217 | GTGGACTCGGTATAAATCAGATTTCTG |
| 04728-R | 158 | CTTTGACTTTCCCACTTGAA | | | |
| 04731-F | 159 | ATACTGTCCTGAGCCTGCTA | | | |
| 04732-R | 160 | AAGTCTGACACTGCTGTTTTCT | 04787 | 218 | CTGGAGCAGGATTAGGTGGTT |
| 0619-F | 161 | GGTGTAGGGTAGCTTGAGATCAG | | | |
| 0620-R | 162 | AAAAGAACAGAAGGGACGAAGG | | | |
| 04741-F | 163 | AACTCACAGTACCACCTTTCAG | 04792 | 219 | GTTCCATCTCCTGCTGGTGA |
| 04742-R | 164 | GATGTAACAAGAACAAAGTGGTC | 07090 | 220 | GTGTGTTCATGTGGGTTGGAC |
| 04743-F | 165 | GTTCTTGTTACATCCAGCAATAG | 04793 | 221 | CTGGTGTCCTCGTCTTGCCA |
| 04744-R | 166 | GGTGTCAAAGTCAGAGAGAGTAA | 07091 | 222 | GTCCAGGAGCCATTTCATATAGACA |
| 04747-F | 167 | TCAGACTAGAATATTTTCACAGC | 04795 | 223 | CCACAACCAAATGAGTCTGCAAATA |
| 04748-R | 168 | TGTCCCTGAATTAGCCATAG | 07093 | 224 | TGGTGTGTGTCCTG |
| 04757-F | 169 | GCTGAATTATTTACCTTCTTCAA | 04800 | 225 | CTGTCATAGGACAGGGTTTAAGACT |
| 04758-R | 170 | AATCTTTATGATGCACTGTGTCT | 07094 | 226 | CCACCAGACTTTAAACCAGAGGTTTA |
| 04771-F | 171 | GGATCGAATTTAACAACGTAATA | | | |
| 04772-R | 172 | CAAAAACTGTAAATTGTAGGAAGA | 04807 | 227 | GGAAGATGCAAAGAAAGAAAGATACTCA |
| 04775-F | 173 | TGGAGATACAGAGATCTTAGGTG | 04809 | 228 | GCTTTGACCCTAGTTTTTGTTCGTG |
| 04776-R | 174 | GAAGCAATAGCAAAGACTCCT | 07095 | 229 | CTCAATCAATAAGAATATGGCCTTGGAG |
| 04779-F | 175 | CAACAATCTTCCTGTGACTTG | 04811 | 230 | CCCAGTGGTGCTTCAGCT |
| 04780-R | 176 | GCTCTTGTACCTTCCCAATC | | 231 | |

In one embodiment of the set of target nucleic acids of this invention, (i) the first target nucleic acid contains SEQ ID NO: 1, 2, 3, 4, 5, or 6; (ii) the second target nucleic acid contains SEQ ID NO: 7, 8, 9, 10, 11, 12, or 13; (iii) the third target nucleic acid contains SEQ ID NO: 14, 15, 16, 17, 18, 19, 20, 21, or 22; (iv) the fourth target nucleic acid contains SEQ ID NO: 23, 24, 25, 26, 27, 28, 29, or 30; (v) the fifth target nucleic acid contains SEQ ID NO: 31, 32, 33, 34, 35, 36, 37, 38, 39, or 40; (vi) the sixth target nucleic acid contains SEQ ID NO: 41, 42, 43, or 44; (vii) the seventh target nucleic acid contains SEQ ID NO: 45, 46, 47, 48, 49, 50, 51, or 52; and (viii) the eighth first target nucleic acid contains SEQ ID NO: 53, 54, 55, 56, 57, 58, 59, 60, 61, 62, 63, 64, 65, 66, 67, 68, 69, 70, 71, 72, 73, or 74. For the oligo-nucleotides, (i) the oligo-nucleotides in the first pair of primers are, SEQ ID NOs: 75 and 76, respectively; SEQ ID NOs: 77 and 78, respectively; or SEQ ID NOs: 79 and 80, respectively; (ii) the oligo-nucleotides in the second pair of primers are, SEQ ID NOs: 81 and 82, respectively; SEQ ID NOs: 81 and 177, respectively; SEQ ID NOs: 83 and 84, respectively; SEQ ID NOs: 83 and 178, respectively; SEQ ID NOs: 85 and 86, respectively; SEQ ID NOs: 87 and 88, respectively; SEQ ID NOs: 89 and 90, respectively; SEQ ID NOs: 89 and 181, respectively; SEQ ID NOs: 91 and 92, respectively; SEQ ID NOs: 93 and 94, respectively; SEQ ID NOs: 179 and 180, respectively; SEQ ID NOs: 182 and 183, respectively; or SEQ ID NOs: 184 and 185, respectively; (iii) the oligo-nucleotides in the third pair of primers are, SEQ ID NOs: 95 and 96, respectively; (iv) the oligo-nucleotides in the fourth pair of primers are, SEQ ID NOs: 97 and 98, respectively; SEQ ID NOs: 186 and 98, respectively; SEQ ID NOs: 99 and 100, respectively; SEQ ID NOs: 99 and 187, respectively; SEQ ID NOs: 101 and 102, respectively; SEQ ID NOs: 101 and 188, respectively; SEQ ID NOs: 103 and 104, respectively; SEQ ID NOs: 103 and 189, respectively; SEQ ID NOs: 105 and 106, respectively; SEQ ID NOs: 105 and 190, respectively; SEQ ID NOs: 107 and 108, respectively; SEQ ID NOs: 191 and 108, respectively; SEQ ID NOs: 109 and 110, respectively; or SEQ ID NOs: 192 and 110, respectively; (v) the oligo-nucleotides in the fifth pair of primers are, SEQ ID NOs: 111 and 112, respectively; SEQ ID NOs: 113 and 114, respectively; SEQ ID NOs: 115 and 116, respectively; SEQ ID NOs: 115 and 195, respectively; SEQ ID NOs: 117 and 118, respectively; SEQ ID NOs: 119 and 120, respectively; SEQ ID NOs: 121 and 122, respectively; SEQ ID NOs: 123 and 124, respectively; or SEQ ID NOs: 193 and 194 respectively; (vi) the oligo-nucleotides in the sixth pair of primers are, SEQ ID NOs: 125 and 126, respectively; SEQ ID NOs: 125 and 196, respectively; SEQ ID NOs: 127 and 128, respectively; SEQ ID NOs: 197 and 128, respectively; SEQ ID NOs: 129 and 130, respectively; SEQ ID NOs: 129 and 198, respectively; SEQ ID NOs: 131 and 132, respectively; or SEQ ID NOs: 199 and 200, respectively; (vii) the oligo-nucleotides in the seventh pair of primers are, SEQ ID NOs: 133 and 134, SEQ ID NOs: 201 and 134, respectively; SEQ ID NOs: 135 and 136, respectively; SEQ ID NOs: 202 and 136, respectively; SEQ ID NOs: 137 and 138, respectively; SEQ ID NOs: 203 and 138, respectively; SEQ ID NOs: 139 and 140, respectively; SEQ ID NOs: 204 and 140, respectively; SEQ ID NOs: 141 and 142, respectively; SEQ ID NOs: 205 and 142, respectively; SEQ ID NOs: 143 and 144, respectively; SEQ ID NOs: 206 and 144, respectively; SEQ ID NOs: 145 and 146, respectively; SEQ ID NOs: 145 and 207, respectively; SEQ ID NOs: 147 and 148, respectively; or SEQ ID NOs: 208 and 148, respectively; and (viii) the oligo-nucleotides in the eighth pair of primers are, SEQ ID NOs: 149 and 150, respectively; SEQ ID NOs: 151 and 152, respectively; SEQ ID NOs: 153 and 154, respectively; SEQ ID NOs: 155 and 156, respectively; SEQ ID NOs: 157 and 158, respectively; SEQ ID NOs: 217 and 158, respectively; SEQ ID NOs: 159 and 160, respectively; SEQ ID NOs: 159 and 218, respectively; SEQ ID NOs: 161 and 162, respectively; SEQ ID NOs: 163 and 164, respectively; SEQ ID NOs:163 and 227, respectively; SEQ ID NOs: 165 and 166, respectively; SEQ ID NOs: 167 and 168, respectively; SEQ ID NOs: 169 and 170, respectively; SEQ ID NOs: 171 and 172, respectively; SEQ ID NOs: 173 and 174, respectively; SEQ ID NOs: 175 and 176, respectively; SEQ ID NOs: 209 and 210, respectively; SEQ ID NOs: 211 and 212, respectively; SEQ ID NOs: 213 and 214, respectively; SEQ ID NOs: 215 and 216, respectively; SEQ ID NOs: 219 and 220, respectively; SEQ ID NOs: 221 and 222, respectively; SEQ ID NOs: 223 and 224, respectively; SEQ ID NOs: 225 and 226, respectively; SEQ ID NOs: 228 and 229 respectively; or SEQ ID NOs: 230 and 176, respectively.

In an preferred embodiment of the set of target nucleic acids of this invention, the first target nucleic acid contains SEQ ID NO: 1, 2, or 3; (b) the second target nucleic acid contains SEQ ID NO: 7, 8, 9, or 10; (c) the third target nucleic acid contains SEQ ID NO: 14 or 15; (d) the fourth target nucleic acid contains SEQ ID NO: 23, 24, 25, 26, 27, or 28; (e) the fifth target nucleic acid contains SEQ ID NO: 31, 32, 33, or 34; (f) the sixth target nucleic acid contains SEQ ID NO: 41, 42, or 43; (g) the seventh target nucleic acid contains SEQ ID NO: 45, 46, or 47; and (h) the eighth target nucleic acid contains SEQ ID NO: 53, 55, 56, or 57. For the oligo-nucleotides, (a) the oligo-nucleotides in the second pair of primers are, respectively, SEQ ID NOs: 81 and 82, SEQ ID NOs: 81 and 177, SEQ ID NOs: 83 and 84, SEQ ID NOs: 83 and 178, SEQ ID NOs: 85 and 86, SEQ ID NOs: 87 and 88, or SEQ ID NOs: 179 and 180; (b) the oligo-nucleotides in the fourth pair of primers are, respectively, SEQ ID NOs: 97 and 98, SEQ ID NOs: 186 and 98, SEQ ID NOs: 99 and 100, SEQ ID NOs: 99 and 187, SEQ ID NOs: 101 and 102, SEQ ID NOs: 101 and 188, SEQ ID NOs: 103 and 104, SEQ ID NOs: 103 and 189, SEQ ID NOs: 105 and 106, or SEQ ID NOs: 105 and 190; (c) the oligo-nucleotides in the fifth pair of primers are, respectively, SEQ ID NOs: 111 and 112, SEQ ID NOs: 113 and 114, SEQ ID NOs: 115 and 116, SEQ ID NOs: 115 and 195, SEQ ID NOs: 117 and 118, or SEQ ID NOs: 193 and 194; (d) the oligo-nucleotides in the sixth pair of primers are, respectively, SEQ ID NOs: 125 and 126, SEQ ID NOs: 125 and 196, SEQ ID NOs: 127 and 128, SEQ ID NOs: 197 and 128, SEQ ID NOs: 129 and 130, or SEQ ID NOs: 129 and 198; (e) the oligo-nucleotides in the seventh pair of primers are, respectively, SEQ ID NOs: 133 and 134, SEQ ID NOs: 201 and 134, SEQ ID NOs: 135 and 136, SEQ ID NOs: 202 and 136, SEQ ID NOs: 137 and 138, or SEQ ID NOs: 203 and 138; and (f) the oligo-nucleotides in the eighth pair of primers are, respectively, SEQ ID NOs: 149 and 150, SEQ ID NOs: 151 and 152, SEQ ID NOs: 153 and 154, SEQ ID NOs: 209 and 210, SEQ ID NOs: 211 and 212, or SEQ ID NOs: 213 and 214.

Another aspect of this invention features a set of nucleic acids comprising one or more of the above-described first, second, third, fourth, fifth, sixth, seventh, and eighth pairs of primers.

A further aspect of this invention features a method of evaluating responsiveness of a subject to a drug. The method includes (1) providing a nucleic acid sample from a subject; (ii) determining a single nucleotide polymorphism genotype (SNP genotype) of a gene group that contains one or more of the human ADAR, CASP5, FGFI, ICSBP1, IFI44, PIK3CG, TAP2, and TGFBRAP1 genes; and (iii) comparing the single nucleotide polymorphism genotype with a predetermined SNP genotype. A subject is predicted to be responsive or non-responsive to the drug if the SNP genotype is identical to a predetermined SNP genotype.

A "genotype" refers to a specific allelic composition of an organism, a genome, or a part of a genome. In particular, this term refers to alleles of a particular gene or set of genes. A single nucleotide polymorphism or SNP genotype refers to the SNP composition of a gene or set of genes. It is presented as a string of nucleotides. For example, a region of human FGF1 gene on each chromosome contains two SNP sites (VGV567 and VGV679). If the two chromosomes of a subject have (1) C and T at the VGV567 sites and (2) A and A at the VGV567 sites, the FGF VGV567/VGV679 SNP genotype of this subject is represented as "CTAA."

In one embodiment, the aforementioned nucleic acid sample contains one or more of the above-described SNP-containing target nucleic acids, which can be obtained from amplification of the corresponding human gene nucleic acid template with a pair of primers. The method can be used to evaluate drug responsiveness of a subject that has or is suspected of having a liver disorder, such as hepatitis (e.g., hepatitis C), liver fibrosis, or liver cirrhosis. Examples of a drug include type I interferon (e.g., interferon-alpha and interferon-beta), ribavirin, or their combination. In one example, a subject is predicted to be responsive or non-responsive to type I interferon if his or her SNP genotype is identical to a predetermined SNP genotype such as one of those reference genotypes listed in Table 4 in Example 1 below. A reference genotype refers to a SNP genotype known to be associated with the responsiveness or non-responsiveness to a certain drug. It can be determined in the manner described in Example 1 below.

The details of one or more embodiments of the invention are set forth in the accompanying description below. Other advantages, features, and objects of the invention will be apparent from the detailed description and the claims.

DETAILED DESCRIPTION

This invention relates to nucleic acids and a method of using the nuclei acids for predicting a subject's responsiveness to a drug based on an SNP genotype of the subject. The method requires determining a subject's SNP genotype of a gene or a set of genes and predicting the subject's responsiveness to the drug by comparing the SNP genotype with reference genotypes known to be associated with responsiveness or non-responsiveness to the drug.

One can select a gene or set of genes that encode proteins involved in the metabolism or signal transduction pathway of the drug of interest. For example, interferon (IFN) or ribavirin is often used in treating hepatitis C. Genes encoding proteins involved in IFN signaling pathways or immunomodulation can be selected for SNP genotyping. As demonstrated in Example 1 below, the SNP genotypes of a set of certain genes showed statistically significant differences between subjects responsive to IFN/ribavirin and subjects non-responsive to IFN/ribavirin. To predict a subject's responsiveness to IFN/ribavirin, one can determine the subject's corresponding SNP genotype of one or more of these genes.

Many technologies known in the art can be used to genotype SNPs (see, e.g., Kwok, Pharmacogenomics, 2000, vol 1, pp 95-100. "High-throughput genotyping assay approaches"). These technologies are based on direct sequencing, allele specific oligonucleotide hybridization, oligonucleotide elongation by dideoxynucleotides or ddNTPs optionally in the presence of deoxynucleotides, ligation of allele specific oligonucleotides, or cleavage of allele specific oligonucleotides. Each of these technologies can be coupled to a detection system such as measurement of direct or polarized fluorescence, or mass spectrometry.

The genotyping assays can be carried out on a product obtained from amplification of the DNA of a subject. This product and corresponding primers are selected to cover a polynucleotide region containing a SNP of interest. Amplification techniques known in the art include, but are not limited to, cloning, polymerase chain reaction (PCR), polymerase chain reaction of specific alleles (ASA), ligase chain reaction (LCR), nested polymerase chain reaction, self sustained sequence replication (Guatelli, et al., 1990, Proc. Natl. Acad. Sci. USA 87:1874-1878), transcriptional amplification system (Kwoh, et al., 1989, Proc. Natl. Acad. Sci. USA 86:1173-1177), and Q-Beta Replicase (Lizardi, et al., 1988, Bio/Technology 6:1197).

Amplification products can be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, primer extension, sequencing, hybridization, and the like. PCR based amplification techniques include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection techniques, e.g., microarraies, allow the differential detection of multiple PCR products in a sample simultaneously.

After determining a subject's SNP genotype, one can compare it with a reference genotype known to be associated with responsiveness or non-responsiveness to a drug. If the SNP genotype is identical to a reference genotype associated with responsiveness (or non-responsiveness), the subject is predicted to be responsive (or non-responsive). When comparing with reference SNP genotypes of more than one gene, one might obtain contradictory conclusions. In this case, one should take into account of the weight, i.e., prediction power, of each gene. Table 4 in Example 1 below lists exemplary reference SNP genotypes of 8 genes and corresponding weights.

For high throughput comparison, one can incorporate reference SNP genotypes of all genes of interest and the corresponding weights into a logical formula, which has a number of variables corresponding to the genes, respectively. After substituting a subject's SNP genotype of each gene for each variable, one can obtain a predicting result returned from the formula. An exemplary logical formula is shown below:

$$p = \frac{\exp(\sum (\text{gene} \times \text{weight}))}{1 + \exp(\sum (\text{gene} \times \text{weight}))}$$

In the formula, "p" stands for the probability of a subject to be responsive to a treatment. "Gene" is a value (e.g., +1, −1, or 0) for a reference SNP genotype of a gene that is associated with the responsiveness or non-responsiveness to a drug. "Weight" represents" the weight/prediction power of each gene as mentioned above.

One can obtain reference SNP genotypes in a manner similar to that described in Example 1 below. More specifically, one can (1) select a sample group of subjects who are known to be responsive or non-responsive to a drug of interest, (2) SNP type a set of candidate genes, and (3) identify the degree of association between an SNP genotype and a responding status using statistic methods known in the art. The genotyping data is then analyzed to estimate the distribution frequency of the different alleles observed in the studied sample. Calculation of the allelic frequencies can be carried out with the assistance of a software program such as SAS® statistical package version 8, SAS-suite® (SAS) or SPLUS® (MathSoft). Comparison of the allelic distributions of a SNP across different ethnic groups can also be carried out by means of the software ARLEQUIN® and SAS-suite®.

The above-described methods and nucleic acids can be used to predict a hepatitis C patient's responsiveness to IFN. They can also be used in predicting IFN responsiveness of a subject that has or is suspected of having disorders that can be treated by IFN. Examples of these disorders include (1) diseases caused by viruses, such as hepatitis (A, B, C, D, E, F, G types) virus, HIV, influenza virus, herpes virus, adenovirus, human polyomavirus, human papilloma virus, human parbovirus, Mumps virus, human rotavirus, enterovirus, Japanese B Encephalitis virus, dengue virus, rubella virus, and HTLV; (2) diseases caused by bacteria, such as *Staphylococcus aureus*, hemolytic *streptococcus*, pathogenic *Escherichia coli*, enteritis *vibrio, Helicobacter pylori, Campylobacter, Vibrio cholerae*, dysentery bacilli, salmonellae, Yelsinia, *Neisseria gonorrhoeae, Listeria, Leptospira, Legionella*, spirochete, *Mycoplasma pneumoniae*, rickettsiae, chlamydiae, malaria plasmodia, dysentery amoeba, and pathogenic fungi; (3) diseases caused by parasites and Eumycetes, and (4) oncological diseases, such as retinoblastoma, Wilm's tumor, familial colonic polyposis, hereditary non polyposis colon cancer, neurofibromatosis, familial chest cancer, xeroderma pigmentosum, blain cancer, oral cancer, esophageal cancer, stomach cancer, colon cancer, liver cancer, pancreatic cancer, lung cancer, thyroid cancer, mammary gland tumor, urinary tumor, virilia tumor, muliebria tumor, skin tumor, osteosarcoma, osteochondrosarcoma, leukemia, lymphoma, and solid tumor.

In addition, as shown in Example 2 below, SNPs of 8 genes were used to accurately predict patients' responsiveness to drugs. The results indicate that the 8 genes (i) are associated with the drug responsiveness and (ii) play important roles in the metabolism or signal transduction pathways of a drug, such as IFN or ribavirin. Accordingly, these genes and SNPs can be used as targets for drug development and as genetic markers for molecular diagnosis, respectively. Indeed, a compound that (i) binds to a protein encoded by one of the genes or (ii) regulates the expression level or activity of the protein is a drug candidate for treating one of the above-mentioned disorders, e.g., a viral infection, such as hepatitis C. Thus, within the scope of this invention is a method for identifying a compound or composition for treating one of the above-mentioned disorders, such as an infection with a virus, e.g., hepatitis virus. The method includes (1) obtaining a first polypeptide that contains a sequence encoded by one of the aforementioned 8 genes; (2) contacting a compound with the first polypeptide; and (3) detecting a binding between the first polypeptide and the compound. The compound is determined to be effective in treating the disorder if the compound binds to the first polypeptide, but not to a second polypeptide that is identical to the first polypeptide, except that the second polypeptide does not have the sequence encoded by one of the aforementioned 8 genes. Also within the scope of this invention is a method for identifying a compound for treating one of the above-mentioned disorders, e.g., a viral infection The method includes (1) obtaining a first system, e.g., a cell, containing or capable of expressing a polypeptide encoded by one of the 8 genes; (2) incubating the first system in a medium containing a compound; and (3) determining an expression or activity level of the polypeptide. The compound is determined to be effective in treating the disorder if the expression or activity level differs from that determined in the same manner from a second system except that the second system is incubated in a medium free of the compound.

The two specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

In this example, genetic markers related to IFN signaling pathways or immunomodulation were analyzed for negative or positive association with IFN/ribavirin treatment for chronic hepatitis C(CHC).

Subjects

Blood samples were collected from 221 chronic hepatitis C patients at National Taiwan University Hospital, Kaohsiung Medical University Hospital, and Tri-Service General Hospital in Taiwan. Informed consent and medical record history were obtained from each patient. All of the patients had received IFN-α (3-5 MU 3 time/per week) and ribavirin (1200 mg/per day) combination therapy for 6-12 months and were followed up for at least 6 months. Patients that showed HCV RNA (+) to HCV RNA (−) conversion 6 months after treatment were defined as "sustained responders (SR)" to this combination treatment. Those still remained HCV RNA (+) were defined as "non-responders (NR)."

Genotyping

Genomic DNAs were extracted from each of the blood samples by standard techniques. The quality of the extracted genomic DNAs was checked by agarose gel electrophoresis analysis and stored at −80° C. until use. More than 1,500 SNPs in 150 candidate genes were SNP genotyped.

SNP genotyping was conducted by DNA sequencing. More specifically, fragments of candidate genes were amplified by the PCR reaction. The reaction mixture contained Tris-HCl 100 mM (pH 8.3), KCl 50 mM, $MgCl_2$ 2.5 mM, 20 ng genomic DNA, 0.2 mM dNTP mixture, each of 0.2 µM forward and reversed primers, 5 U of VioTaq DNA polymerase (VIOGENE) and 0.025 U of Pfu DNA polymerase (Stratagene) in a total volume of 50 µL reaction. The PCR was performed using a touch-down program including an initial denaturing at (i) 94° C. for 4 minutes; (ii) 10 cycles of: melting at 94° C. for 40 seconds, annealing at 70° C. with 1° C. decrement per cycle for 40 seconds, and extending at 72° C. for 1 minute 30 seconds; (iii) 25 cycles of: melting at 94° C. for 40 seconds, annealing at 60° C. for 40 seconds, and extending at 72° C. for 1 minute 30 seconds; and (iv) one cycle of final extension at 72° C. for 10 minutes. The amplification was carried out on 2700 PCR machines (ABI). The amplified products were purified by membrane ultra-filtration with a MultiScreen PCR plate (Millipore) according to the manufacture's instructions. PCR products from each gene were then sequenced by a sequencer. Each sequencing reaction mixture contained corresponding PCR products, Big Dye Terminator Ready-Reaction-Premix, and 10 pmol of a sequencing primer. The sequencing was performed using a program of 28 cycles at 94° C. for 30 seconds, 48° C. for 30 seconds, and 58° C. for 2 minutes. After the sequencing, the reaction products were loaded on an ABI 3700 capillary sequencer. DNA sequence date and track were collected by ABI DNA Sequence Analyzer. Phrad was used to perform base calling and sequencing assembling. The initial identification of potential SNP sites was performed by Polyphred (Department of Genome Sciences, University of Washington, Seattle, Wash.). PolyPhred is a software program that compares fluorescence-based sequences across traces obtained from different individuals to identify heterozygous sites for single nucleotide substitutions. Its functions are integrated with the use of three other programs also from the same source: Phred (a base-caller program), Phrap (an assembler program), and Consed (a Unix-based graphical editor and automated finishing program for Phrap Sequence Assemblies). PolyPhred identifies potential heterozygotes using the base calls and peak information provided by Phred and the sequence alignments provided by Phrap. Potential heterozygotes identified by PolyPhred are marked for rapid inspection using the Consed tool. Finally, the genotype of each tested individual was determined by computer software and confirmed manually.

Alternatively, SNP genotyping was conducted by the Template-directed Dye Terminator Incorporation assay with Fluorescent Polarization detection (FP-TDI, Washington University School of Medicine, St. Louis, Mich.). Primers were designed for each SNP site of the candidate genes. The SNP primers used for genotyping SNPs in the 8 genes described above are listed in Table 2. For each typing, PCR was performed in a total volume of 10 µl of 1×PCR buffer (Applied Biosystems), 2.5 mM $MgCl_2$, 50 M dNTP, 0.1 M each of forward and reverse primers, and 0.2 U AmpliTaq Gold DNA polymerase. The thermal cycle condition for the PCR reaction was: activation step at 94° C. for 10 minutes, 35 cycles at 95° C. for 10 seconds, 55° C. for 20 seconds, and 72° C. for 30 seconds, ending with 10 minutes at 72° C. After the PCR reaction, excessive PCR primers and dNTPs were cleansed in a degradation reaction. A PCR clean-up reagent for this degradation reaction contained 1 U shrimp alkaline phosphatase and 1 U *E. Coli* exonuclease I in a shrimp alkaline phosphatase buffer (25 mM Tris-HCl, pH 8.5 and 2.5 mM MgCl2). The reaction was performed at 37° C. for 1 hour, followed by an incubation at 80° C. for 15 minutes. Single-base extension was then performed in a solution containing 1× reaction buffer (Perkin Elmer), 0.25 M SNP primer, 1 µl Acyclo Terminator Mix (Perkin Elmer), and 0.25 U Acyclo-Pol DNA polymerase (Perkin Elmer) under the following conditions: 95° C. for 2 minutes, 25 to 50 cycles of 95° C. for 15 seconds, and 55° C. for 30 seconds. Then, fluorescence-polarization was measured on a Perkin Elmer fluorescence reader to detect the distribution of SNPs of 8 genes.

Estimation of SNP Haplotype and Frequencies

In this study, a computer program PHASE was used to estimate haplotypes and their frequencies on the basis of unphased genotype data. A Bayesian algorithm was used with this program PHASE to examine the unknown haplotypes as unobserved random quantities for evaluating their frequencies and the conditional distribution of multilocus haplotypes in diploid populations. The D' and $r^2$ measures were used to analyze linkage disequilibrium between pairs of SNPs.

Statistical Analysis

Statistical analyses were performed using the SAS statistical package version 8®. The $\chi^2$ or Fisher exact test was used to compare the genotypes and allele frequencies between SR and NR of each SNP. The $\chi^2$ or Fisher exact test was also performed to evaluate the combined genotypes of multiple SNPs in the same gene or pathway. Multiple-logistic regression was performed to evaluate whether there was a difference in response for each SNP after adjustment for age, gender, living habits, and related viral factors. All statistical tests were 2-tailed and P-values less than 0.05 were considered statistically significant.

Results

It was shown that a collection of SNPs of 8 genes, i.e., ADAR, CASP5, FGF1, ICSBP1, IFI44, PIK3CG, TAP2, and TGFBRAP1, were strongly associated with the responsiveness in hepatitis C patients. These 8 genes were selected by association analysis of responsive status using major haplotype frequencies from each gene in the candidate gene pool. A set of SNPs of the 8 genes that retained most of the information available in the full haplotype (htSNP) of each gene were selected and listed in Table 3.

TABLE 3

Selected Sets of SNPs

| Gene | SNP ID |
|---|---|
| ADAR | VGV1473, VGV1600, VGV1798 |
| CASP5 | rs518604, rs2282658, rs484345, rs1699087 |
| FGF1 | VGV567, VGV679 |
| ICSBP1 | rs385989, rs305067, VGV1824, VGV1826, rs305088, VGV1827 |
| IFI44 | VGV199, VGV2188, VGV2191, VGV33 |
| PIK3CG | rs1526083, rs3779501, rs2037718 |
| TAP2 | rs1871665, rs2071543, rs1800453 |
| TGFBRAP1 | VGV2200, VGV2204. VGV2197, VGV2325 |

Then, the SNP genotypes associated with responsiveness to the IFN-α/ribavirin treatment or non-responsiveness to the treatment were obtained. The SNP genotypes that were associated with responsiveness ("R") or non-responsiveness ("NR"), i.e., reference genotypes, were summarized in Table 4 below. Also included in Table 4 was the weight of each gene. Based on the weight, the prediction power, i.e., priority, of each gene was also determined and shown in Table 4

TABLE 4

Reference Genotypes and Weights

| Priority | GENE | Reference Genotype | Responsiveness | Weight | SEQ ID NO: |
|---|---|---|---|---|---|
| 1 | TGFBRAP1 | GCCCCTTT | R | 11.7689 | |
|  |  | CCCCTTTT | R |  |  |
|  |  | CCCTCTCT | R |  |  |
|  |  | CCTTCCCC | R |  |  |
| 5 | PIK3CG | AACTGG | NR | 2.5411 | |
| 8 | ICSBP1 | GGCCGGCGTTCC | R | 0.122 | 231 |
|  |  | GTGGGGAACCGG | R |  | 232 |
|  |  | TTCCGGAATCGA | R |  | 233 |
|  |  | TTCCGGAATCGG | R |  | 234 |
|  |  | TTCCGGAATTGG | R |  | 235 |
|  |  | TTCGGGAACCGG | R |  | 236 |
|  |  | TTCGGGAATCGG | R |  | 237 |
|  |  | TTGGGGAACCGG | NR |  | 238 |
| 3 | IFI44 | GGTTAAAG | R | 2.937 | |
|  |  | GGTTAGGG | NR |  |  |
|  |  | GTTTAAAA | R |  |  |
|  |  | GTTTAAAG | R |  |  |
|  |  | GTTTAGGG | NR |  |  |
| 4 | TAP2 | CACTCC | R | 2.6099 | |
| 2 | ADAR | CCAACC | R | 2.9426 | |
|  |  | CTAGCC | NR |  |  |
|  |  | TTGGCC | NR |  |  |
|  |  | TTGGCT | NR |  |  |
| 6 | CASP5 | AACCAACA | NR | 1.5063 | |
|  |  | AACGGACA | NR |  |  |

TABLE 4-continued

Reference Genotypes and Weights

| Priority | GENE | Reference Genotype | Responsiveness | Weight | SEQ ID NO: |
|---|---|---|---|---|---|
| | | GACCAACA | NR | | |
| | | GACCAACC | NR | | |
| | | GACCGACA | R | | |
| | | GACCGGAA | R | | |
| | | GACGGACA | R | | |
| | | GACGGGAA | R | | |
| 7 | FGF1 | CTAA | R | 1.1484 | |

EXAMPLE 2

The just-described set of SNPs of the 8 genes was used to predict the responsiveness of 221 patients to IFN α/ribavirin treatment in a blind test. The SNP genotypes of the 221 patients were determined by the method described above. Different numbers of patients were selected randomly for each gene. The responsiveness to IFN α/ribavirin treatment were predicted based on the reference SNP genotypes of ADAR, CASP5, FGF1, ICSBP1, IFI44, PIK3CG, TAP2, and TGFBRAP1, respectively. The results are shown in Table 5 below.

TABLE 5

Predicting Responsiveness to IFN-α/ribavirin

| Gene | Patients Included | Correctly Predicted | Accuracy | Coverage |
|---|---|---|---|---|
| ADAR | 60 | 48 | 80.00% | 27.15% |
| CASP5 | 54 | 41 | 75.90% | 24.43% |
| FGF1 | 102 | 67 | 65.70% | 46.15% |
| ICSBP1 | 81 | 64 | 79.00% | 36.65% |
| IFI44 | 62 | 49 | 79.00% | 28.05% |
| PIK3CG | 15 | 11 | 73.30% | 6.78% |
| TAP2 | 9 | 6 | 66.70% | 4.07% |
| TGFBRAP1 | 38 | 31 | 81.60% | 17.19% |

The results show that the prediction is highly accurate. The results also indicate that SNPs of the 8 genes are associated with the drug responsiveness and the genes indeed play important roles in the metabolism or signal transduction pathways of an anti-viral drug, such as IFN or ribavirin. Accordingly, the genes and the corresponding SNPs can be used as targets for anti-viral drug development and as genetic markers for molecular diagnosis, respectively.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of evaluating responsiveness of a subject to a drug, comprising
providing a nucleic acid sample from a subject;
determining a single nucleotide polymorphism genotype of a gene group that includes the human ADAR, CASP5, FGF1, ICSBP1, IFI44, PIK3CG, TAP2, and TGFBRAP1 genes; and
comparing the single nucleotide polymorphism genotype of the human ADAR, CASP5, FGF1, ICSBP1, IFI44, PIK3CG, TAP2, and TGFBRAP1 genes with a predetermined single nucleotide polymorphism genotype for each of human ADAR, CASP5, FGF1, ICSBP1, IFI44, PIK1CG, TAP2, and TGFBRAP1 genes,
whereby the subject is predicted to be responsive or non-responsive to the drug if the single nucleotide polymorphism genotype is identical to a predetermined single nucleotide polymorphism genotype of the human ADAR, CASP5, FGF1, ICSBP1, IFI44, PIK3CG, TAP2, and TGFBRAP1 genes.

2. The method of claim 1, wherein the nucleic acid sample comprises:
a first target nucleic acid obtained from amplification of the human ADAR gene nucleic acid template with a first pair of primers, each containing an oligo-nucleotide selected from the ADAR gene region;
a second target nucleic acid obtained from amplification of the human CASP5 gene nucleic acid template with a second pair of primers, each containing an oligo-nucleotide selected from the CASP5 gene region;
a third target nucleic acid obtained from amplification of the human FGF1 gene nucleic acid template with a third pair of primers, each containing an oligo-nucleotide selected from the FGF1 gene region;
a fourth target nucleic acid obtained from amplification of the human ICSBP1 gene nucleic acid template with a fourth pair of primers, each containing an oligo-nucleotide selected from the ICSBP1 gene region;
a fifth target nucleic acid obtained from amplification of the human IFI44 gene nucleic acid template with a fifth pair of primers, each containing an oligo-nucleoticle selected from the IFI44 gene region;

a sixth target nucleic acid obtained from amplification of the human PIK3CG gene nucleic acid template with a sixth pair of primers, each containing an oligo-nucleotide selected from the PIK3CG gene region;

a seventh target nucleic acid obtained from amplification of the human TAP2 gene nucleic acid template with a seventh pair of primers, each containing an oligo-nucleotide selected from the TAP2 gene region; and an eighth target nucleic acid obtained from amplification of the human TGFBRAP1 gene nucleic acid template with a eighth pair of primers, each containing an oligonucleotide selected from the TGFBRAP1 gene region;

wherein each target nucleic acid has a nucleotide at a single nucleotide polymorphism site and is 20-1,000 nucleotides in length.

3. The method of claim 2, wherein
the first target nucleic acid contains SEQ ID NO:2 SEQ ID NO: 1, 2, 3, 4, 5, or 6;
the second target nucleic acid contains SEQ ID NO: 7 SEQ ID NO: 7, 8, 9, 10, 11, 12, or 13;
the third target nucleic acid contains SEQ ID NO: 14 SEQ ID NO: 14, 15, 16, 17, 18, 19, 20, 21, or 22;
the fourth target nucleic acid contains SEQ ID NO: 26 SEQ ID NO: 23, 24, 25, 26, 27, 28, 29, or 30;
the fifth target nucleic acid contains SEQ ID NO: 32 SEQ ID NO: 31, 32, 33, 34, 35, 36, 37, 38, 39, or 40;
the sixth target nucleic acid contains SEQ ID NO: 42 SEQ ID NO: 41, 42, 43, or 44;
the seventh target nucleic acid contains SEQ ID NO: 46 SEQ ID NO: 45. 46, 47, 48, 49, 50, 51, or 52; and
the eighth target nucleic acid contains SEQ ID NO: 56 SEQ ID NO: 53, 54, 55, 56, 57, 58, 59, 60, 61, 62, 63, 64, 65, 66, 67, 68, 69, 70, 71, 72, 73, or 74.

4. The method of claim 3, wherein
the first target nucleic acid contains SEQ ID NO:2;
the second target nucleic acid contains SEQ ID NO: 7;
the third target nucleic acid contains SEQ ID NO: 14;
the fourth target nucleic acid contains SEQ ID NO: 26;
the fifth target nucleic acid contains SEQ ID NO: 32;
the sixth target nucleic acid contains SEQ ID NO: 42;
the seventh target nucleic acid contains SEQ ID NO: 46; and
the eighth target nuclcic acid contains SEQ ID NO: 56.

* * * * *

UNITED STATES PATENT AND TRADEMARK OFFICE
CERTIFICATE OF CORRECTION

PATENT NO. : 7,405,043 B2  Page 1 of 1
APPLICATION NO. : 10/880315
DATED : July 29, 2008
INVENTOR(S) : Yuchi Hwang It is certified that error appears in the above-identified patent and that said Letters Patent is hereby corrected as shown below:

In Column 99, Line 61, in Claim 1, delete "PIK1CG," and insert -- PIK3CG, --.

In Column 100, Line 59, in Claim 2, delete "thc" and insert -- the --.

In Column 101, Line 1, in Claim 2, delete "oligo-nucleoticle" and insert -- oligo-nucleotide --.

In Column 101, Line 13-14, in Claim 2, delete "oligonucleotide" and insert -- oligo-nucleotide --.

In Column 102, Line 8, in Claim 3, delete "45." and insert -- 45, --.

In Column 102, Line 22, in Claim 4, delete "nuclcic" and insert -- nucleic --.

Signed and Sealed this

Twenty-eighth Day of July, 2009

JOHN DOLL
*Acting Director of the United States Patent and Trademark Office*

SEQUENCE LISTING

<160> NUMBER OF SEQ ID NOS: 230

<210> SEQ ID NO 1
<211> LENGTH: 120
<212> TYPE: DNA
<213> ORGANISM: Homo sapiens

<400> SEQUENCE: 1
tggcgtgaac ccgggaggcg gagcttgcag tgagccgaga tcgcgccact gcactccagc    60
ytgagagaca gagtgatact ccatctctaa atcaatcaat caatcaatca atcaatcaat    120

<210> SEQ ID NO 2
<211> LENGTH: 120
<212> TYPE: DNA
<213> ORGANISM: Homo sapiens

<400> SEQUENCE: 2
agcttcagtg gttttgctct ctgttatgcc cttcagaagc tcctgttttc ctcaatctgt    60

-continued

```
ycactggcct attaggacct acagtgcagg gcctgaccag ctatctgagt gaggtaaagg        120

<210> SEQ ID NO 3
<211> LENGTH: 120
<212> TYPE: DNA
<213> ORGANISM: Homo sapiens

<400> SEQUENCE: 3
ctgaggcagg agaatggcgt gaacccggga ggcggagctt gcagtgagcc gagatcgcgc         60
yactgcactc cagcttgaga gacagagtga tactccatct ctaaatcaat caatcaatca        120

<210> SEQ ID NO 4
<211> LENGTH: 120
<212> TYPE: DNA
<213> ORGANISM: Homo sapiens

<400> SEQUENCE: 4
ctctggctgg gagcagtggc tcacgcctgt aatcccagca ctttgggagg ctgaggtgga         60
yctcacgagg tcaggagatt gagaccatcc tggctaacac ggtgaaaccc catctctact        120

<210> SEQ ID NO 5
<211> LENGTH: 120
<212> TYPE: DNA
<213> ORGANISM: Homo sapiens

<400> SEQUENCE: 5
gggaagggcc ctgctgggta cgtaatcaaa aggtgcctga tgaacccac cccacccaga         60 ygcaaattta cccacaaagg gaggttcttt gaaatggctc cttttccaaag gctgagggac      120

<210> SEQ ID NO 6
<211> LENGTH: 120
<212> TYPE: DNA
<213> ORGANISM: Homo sapiens

<400> SEQUENCE: 6
gattatttct gcatggcagt cattgacagt ttctcctttt aggctgagag aatctccttt         60
yacacagcga ttccctagga aggtgtttaa aacagaaata gaataatgga aggaaaccga       120

<210> SEQ ID NO 7
<211> LENGTH: 120
<212> TYPE: DNA
<213> ORGANISM: Homo sapiens

<400> SEQUENCE: 7
ataacattgc tctttgtagg atcaagtggg atatatgtag aagagggctt gaagttgatc         60
rtttggaaag acagccagta ctgggatcca taaaacttct attcaaaatg ttaaatggat       120

<210> SEQ ID NO 8
<211> LENGTH: 120
<212> TYPE: DNA
<213> ORGANISM: Homo sapiens

<400> SEQUENCE: 8
caaggtggtc tctaacagga tgatgacatg tttactgaaa atgagagttt agaaatgaaa         60
stgtaggtag atcacagata acactgcatg ggccttggag ttgaatatat tctggaaaat       120

<210> SEQ ID NO 9
<211> LENGTH: 120
<212> TYPE: DNA
```

<213> ORGANISM: Homo sapiens

<400> SEQUENCE: 9

| tccaaataat | acttacagtc | aagtggctga | ctcctcctat | ttcatggtca | accaaattgc | 60 |
| rtcattatca | tcatcaacat | caccactatc | attgttgtca | tcattatctt | tattgagcaa | 120 |

<210> SEQ ID NO 10
<211> LENGTH: 120
<212> TYPE: DNA
<213> ORGANISM: Homo sapiens

<400> SEQUENCE: 10

| tgcaggtatc | tgcagctacc | tccttcctgc | cacaacctct | gctgatcaga | aaggttattt | 60 |
| mattttggaa | tttagtgctc | attatatatg | agaattgtac | gtgataaata | atatataatt | 120 |

<210> SEQ ID NO 11
<211> LENGTH: 120
<212> TYPE: DNA
<213> ORGANISM: Homo sapiens

<400> SEQUENCE: 11

| catgggcctt | ggagttgaat | atattctgga | aaatttaaca | tatttatcgt | gttagatgca | 60 |
| rccttacgtt | ttacactggt | gatcttttgg | tccatattga | gaagtgtttg | ggtaaacatt | 120 |

<210> SEQ ID NO 12
<211> LENGTH: 120
<212> TYPE: DNA
<213> ORGANISM: Homo sapiens

<400> SEQUENCE: 12

| tggtcatcca | ttgtattcag | atttctctct | cttgctcaaa | ctcatgatga | cctacctgaa | 60 |
| rtgtgtgcac | ccaggacagt | ccattctctt | gtctagactg | taaattattc | ctactagact | 120 |

<210> SEQ ID NO 13
<211> LENGTH: 120
<212> TYPE: DNA
<213> ORGANISM: Homo sapiens

<400> SEQUENCE: 13

| ggggtctaaa | tgaaaaactt | tgggagaaga | gcaacgtgct | ctgcactgac | cagaagaaag | 60 |
| rcattacttc | agtattttct | gtatatggct | tgattatccc | ttatccaaaa | tgcatgctac | 120 |

<210> SEQ ID NO 14
<211> LENGTH: 120
<212> TYPE: DNA
<213> ORGANISM: Homo sapiens

<400> SEQUENCE: 14

| gtttcgccct | tgtgaggcac | actgggcaat | gctgccattc | ccattccaca | ggtgaggaaa | 60 |
| ytgagtctca | gcgagactaa | atgatttttcc | tgaaaattat | ctgggaacac | tagagacact | 120 |

<210> SEQ ID NO 15
<211> LENGTH: 120
<212> TYPE: DNA
<213> ORGANISM: Homo sapiens

<400> SEQUENCE: 15

| gaaccctagt | aaatagaagt | ttcgcccttg | tgaggcacac | tgggcaatgc | tgccattccc | 60 |
| mttccacagg | tgaggaaact | gagtctcagc | gagactaaat | gatttttcctg | aaaattatct | 120 |

<210> SEQ ID NO 16
<211> LENGTH: 120
<212> TYPE: DNA
<213> ORGANISM: Homo sapiens

<400> SEQUENCE: 16 gggggcttg aagcttcttt cgcagagttt gcaaacagaa agaatgcata atggcaagaa    60
mgttaattgt ccagggctgc tccaggtaga aaggggcaga gtaggcttga actcgagcct   120

<210> SEQ ID NO 17
<211> LENGTH: 120
<212> TYPE: DNA
<213> ORGANISM: Homo sapiens

<400> SEQUENCE: 17
caggtgagga aactgagtct cagcgagact aaatgatttt cctgaaaatt atctgggaac    60
rctagagaca cttcaatttc tagtcaggaa aggactggaa gcgtcccagg gctgggggc   120

<210> SEQ ID NO 18
<211> LENGTH: 120
<212> TYPE: DNA
<213> ORGANISM: Homo sapiens

<400> SEQUENCE: 18
gaggcaattc tgtttctgaa taaccttga aactcagaag ggctctggca gtaccaccac    60
ygggcagaag agggcaacag aaccacattc agggagtaca tccgtgccca ggactcctct   120

<210> SEQ ID NO 19
<211> LENGTH: 120
<212> TYPE: DNA
<213> ORGANISM: Homo sapiens

<400> SEQUENCE: 19
tcacatttag tcagggagca tccgtctcat gcctggccga ggcaattctg tttctgaata    60
mcccttgaaa ctcagaaggg ctctggcagt accaccactg ggcagaagag ggcaacagaa   120

<210> SEQ ID NO 20
<211> LENGTH: 120
<212> TYPE: DNA
<213> ORGANISM: Homo sapiens

<400> SEQUENCE: 20
caaggaatca aaatatctc cttgccaggc cgtgtggatc acatttagtc agggagcatc    60
ygtctcatgc ctggccgagg caattctgtt tctgaataac ccttgaaact cagaagggct   120

<210> SEQ ID NO 21
<211> LENGTH: 120
<212> TYPE: DNA
<213> ORGANISM: Homo sapiens

<400> SEQUENCE: 21
tttcgattgg ctttttagaaa cgctctttct gaaggaagtc ttaacgtgtg actctgtcac    60
ytcagtctct aattatgctc aaactagtga tcaaggaatc aaaatatct ccttgccagg   120

<210> SEQ ID NO 22
<211> LENGTH: 120
<212> TYPE: DNA
<213> ORGANISM: Homo sapiens -continued

<400> SEQUENCE: 22 tttcgattg gcttttagaa acgctctttc tgaaggaagt cttaacgtgt gactctgtca      60
sttcagtctc taattatgct caaactagtg atcaaggaat caaaaatatc tccttgccag    120

<210> SEQ ID NO 23
<211> LENGTH: 120
<212> TYPE: DNA
<213> ORGANISM: Homo sapiens

<400> SEQUENCE: 23
tgacgacatg tgcccaaggt ggtcggggca cagcctggtt ttatacattt tagggagaca     60
kgagacatca atcaatacat gtaagaagta cactggttcc atccagaaag acggggacag   120

<210> SEQ ID NO 24
<211> LENGTH: 120
<212> TYPE: DNA
<213> ORGANISM: Homo sapiens

<400> SEQUENCE: 24
agtgattggc tcaggaaggg gcatgggact gaataatggc caatgagctg agaggaaaaa     60
sacctgctgg ggcttccagg aaggtccctc cttccttgcc acctggtgtg tccagaggat   120

<210> SEQ ID NO 25
<211> LENGTH: 120
<212> TYPE: DNA
<213> ORGANISM: Homo sapiens

<400> SEQUENCE: 25
caccaagaga acatgttcta ggaggcagga agaagcagct cgcagattct taagtctcac     60
rcctagaaac ggacacagca tcacttctac ctatgctgct ggtcaaagca ggcacagagc   120

<210> SEQ ID NO 26
<211> LENGTH: 120
<212> TYPE: DNA
<213> ORGANISM: Homo sapiens

<400> SEQUENCE: 26
gattcttaag tctcacgcct agaaacggac acagcatcac ttctacctat gctgctggtc     60
maagcaggca cagagcccac tggattgaag aaagaggcat agaccccac ctttaaaggg    120

<210> SEQ ID NO 27
<211> LENGTH: 120
<212> TYPE: DNA
<213> ORGANISM: Homo sapiens

<400> SEQUENCE: 27
cgtgcgaggt gctgcgctca cagtattact catgcacctt tctgataaga aaagtgaaaa     60
ygtgaagttg aaaactgaag acgcccagca acttcctgaa tccagccctc cacgtcctgc   120

<210> SEQ ID NO 28
<211> LENGTH: 120
<212> TYPE: DNA
<213> ORGANISM: Homo sapiens

<400> SEQUENCE: 28
actgggaacc tccatagtta ccacatgctg cgctgacttc tctaacacgc tttggccaat     60
ratgtttccc taatcacagc agctcctcat ttagaatgtg ttcttattta ggatgcgttc   120

<210> SEQ ID NO 29
<211> LENGTH: 120
<212> TYPE: DNA
<213> ORGANISM: Homo sapiens

<400> SEQUENCE: 29
atgaaagtgc tgttctcatc acttcctatc catggtccat gctgtccgtg tgacttacca      60
yggtggacgt tgaccttggc cacctggctg gctgttgggt tctccactgg aagtttactc     120

<210> SEQ ID NO 30
<211> LENGTH: 120
<212> TYPE: DNA
<213> ORGANISM: Homo sapiens

<400> SEQUENCE: 30
acctatgctg ctggtcaaag caggcacaga gcccactgga ttgaagaaag aggcatagac      60
ycccaccttt aaagggctga gtgtcagaga acttgtggcc aacattaatc caccacaact     120

<210> SEQ ID NO 31
<211> LENGTH: 120
<212> TYPE: DNA
<213> ORGANISM: Homo sapiens

<400> SEQUENCE: 31
aagccctcaa atcccattcc taatctgatg agtctatgga ccaatttgtg gaggacagta      60
kattaaatag atctgatttt tgccatcaat gtaaggagga taaaaacttg cataccaatt     120

<210> SEQ ID NO 32
<211> LENGTH: 120
<212> TYPE: DNA
<213> ORGANISM: Homo sapiens

<400> SEQUENCE: 32
ggaaaatata tatgatttgc cactagatca agaagtatgg cagtgacaac tcgtttgaca      60
yggttgcacg aaaagatcct gcaaaatcat tttggaggga agcggcttag ccttctctat     120

<210> SEQ ID NO 33
<211> LENGTH: 120
<212> TYPE: DNA
<213> ORGANISM: Homo sapiens

<400> SEQUENCE: 33
cctcagtata aaagctctat cagtaccatg aacaatctca tcataatcac acttaatatc      60
rtttcatata atcacaatca aaactggaaa caattaaaac attttagcat attttatag     120

<210> SEQ ID NO 34
<211> LENGTH: 120
<212> TYPE: DNA
<213> ORGANISM: Homo sapiens

<400> SEQUENCE: 34
aggtggtttc atttgaggcc tcatttgtta ccattgaaat caatgaaggt gactccccat      60
rtcagagaaa ttccagatac taataagtag tccaggggag ttttttgggg agatgagggt     120

<210> SEQ ID NO 35
<211> LENGTH: 120
<212> TYPE: DNA
<213> ORGANISM: Homo sapiens

<400> SEQUENCE: 35

```
ctgtctgcct tgagaactta tgaaccatat ggatccctgg ttcaacaaat acgaattctg    60
ytgctgggtc caattggagc tgggaagtcc agcttttca actcagtgag gtctgttttc   120
```

<210> SEQ ID NO 36
<211> LENGTH: 120
<212> TYPE: DNA
<213> ORGANISM: Homo sapiens

<400> SEQUENCE: 36

```
ggtccaattg gagctgggaa gtccagcttt ttcaactcag tgaggtctgt tttccaaggg    60
yatgtaacgc atcaggcttt ggtgggcact aatacaactg ggatatctga aaggtaagc   120
```

<210> SEQ ID NO 37
<211> LENGTH: 120
<212> TYPE: DNA
<213> ORGANISM: Homo sapiens

<400> SEQUENCE: 37

```
ggggtgtaca aattattgta ttttaaagtc aatcagaata gtttattctt gtattataac    60
mataacagtt cactaattaa attaaattta ggaattgaat tgttaagtta atttggtttt   120
```

<210> SEQ ID NO 38
<211> LENGTH: 120
<212> TYPE: DNA
<213> ORGANISM: Homo sapiens

<400> SEQUENCE: 38

```
cataaatttt agttacctct tccaagaggt ggtttcattt gaggcctcat tgttaccat    60 kgaaatcaat gaaggtgact ccccatgtca gagaaattcc agatactaat aagtagtcca   120
```

<210> SEQ ID NO 39
<211> LENGTH: 120
<212> TYPE: DNA
<213> ORGANISM: Homo sapiens

<400> SEQUENCE: 39

```
tccaagaggt ggtttcattt gaggcctcat tgttaccat tgaaatcaat gaaggtgact    60
ycccatgtca gagaaattcc agatactaat aagtagtcca ggggagtttt tggggagat   120
```

<210> SEQ ID NO 40
<211> LENGTH: 120
<212> TYPE: DNA
<213> ORGANISM: Homo sapiens

<400> SEQUENCE: 40

```
acattgtagt acttgtaaat aactagaaat aacatgattt agtcataatt gtgaaaaata    60
rtaataattt ttcttggatt tatgttctgt atctgtgaaa aataaatttt cttataaaac   120
```

<210> SEQ ID NO 41
<211> LENGTH: 120
<212> TYPE: DNA
<213> ORGANISM: Homo sapiens

<400> SEQUENCE: 41

```
tgttatcaat ggaagccttc tcaaaaggaa ttgatttgca tatgcacagg cactccattc    60
rgttgtcatc aaatgcccctt tgttcagagc ttcatcatcg gcaaaagtag atatgatgaa   120
```

<210> SEQ ID NO 42
<211> LENGTH: 120

<210> SEQ ID NO 42
<211> LENGTH: 120
<212> TYPE: DNA
<213> ORGANISM: Homo sapiens

<400> SEQUENCE: 42
tgctgctttt aaaattatga actatttcaa acttacagaa aagcacagag aacaatgaaa    60
yacctatgca ctcacaagat ttaattgtgt tttttacatt ttatcagttc ttcctcatca   120

<210> SEQ ID NO 43
<211> LENGTH: 120
<212> TYPE: DNA
<213> ORGANISM: Homo sapiens

<400> SEQUENCE: 43
gatcctattt acagcattct atttattaat ttttataaaa acctagttta ttaaaaacta    60
sttacagtaa tatttgattt tttaaagaca attaggtcat ttgtaaataa taagttttcc   120

<210> SEQ ID NO 44
<211> LENGTH: 120
<212> TYPE: DNA
<213> ORGANISM: Homo sapiens

<400> SEQUENCE: 44
gctaggatta tttgcaggtt tggttttttc tcatttgtct gtggcattgg agaatattct    60
yggtttaaac agactaatga cttccttatt gtccctgata ttttgactat cttactattg   120

<210> SEQ ID NO 45
<211> LENGTH: 120
<212> TYPE: DNA
<213> ORGANISM: Homo sapiens

<400> SEQUENCE: 45
ggaaaagagt aatgattctg gaaagaaagg tgataagcct cagagtaaga tcttcaggga    60
ytagcaagat gagctgggaa agaagagtga gagggagaag catacccatc ctgagagagt   120

<210> SEQ ID NO 46
<211> LENGTH: 120
<212> TYPE: DNA
<213> ORGANISM: Homo sapiens

<400> SEQUENCE: 46
cctccactcc tcagcgcccg cctccctgca tccctagggg cttccctact gccccgacct    60
kcattccccg gggtaaagcg agctctggag atcgcataga gaaactgtag tgtcctgggt   120

<210> SEQ ID NO 47
<211> LENGTH: 120
<212> TYPE: DNA
<213> ORGANISM: Homo sapiens

<400> SEQUENCE: 47
aatgctcggg ccaacgccac tgcctgtcgc tgaccccctg acagctggct cccagcctcg    60
yctacctctg cagagcaaag ggccaagatg agaacggtat agccacatgt gtgcacgcat   120

<210> SEQ ID NO 48
<211> LENGTH: 120
<212> TYPE: DNA
<213> ORGANISM: Homo sapiens

<400> SEQUENCE: 48
aactgtgaga aataaatttc tgttcttcat aaattaccct atctcgtgta tcttgttaca    60
mtaacacaaa tggactaaga cagagagcat aaggcttggg ggaagaaggg tacacttctt    120

<210> SEQ ID NO 49
<211> LENGTH: 120
<212> TYPE: DNA
<213> ORGANISM: Homo sapiens

<400> SEQUENCE: 49
tcagatcatc ttcttctgtg agggctgcag cttccatgta gttgggagat acaggaatta    60
ytattcctgt tttatgaata aaggacattt gtgggagaga aaggaatcag gccagagttc    120

<210> SEQ ID NO 50
<211> LENGTH: 120
<212> TYPE: DNA
<213> ORGANISM: Homo sapiens

<400> SEQUENCE: 50
cctgatttaa gcaaagtata ataaacacac tcatacacat atactacatg gataccacaa    60
rtggaaattt gacaattgac tatttgataa attttaagaa ctactgttaa ttttttggtg    120

<210> SEQ ID NO 51
<211> LENGTH: 120
<212> TYPE: DNA
<213> ORGANISM: Homo sapiens

<400> SEQUENCE: 51
tcatagtcaa ttactctgtg ttgggtctac accacatctg cacatactat gagcccttcc    60
rttggagata attttcactt gcggagctgc ttcacttcta cctgtaggag cctcatctcc    120

<210> SEQ ID NO 52
<211> LENGTH: 120
<212> TYPE: DNA
<213> ORGANISM: Homo sapiens

<400> SEQUENCE: 52
attggctcat actactgtgg gagctggcac ggtcgaaatc tgcaggtagg ctggagaccc    60
rggaagagct gatgttgcgg cttgagtctg aaggtggtcc agaggcagaa ttccctcttc    120

<210> SEQ ID NO 53
<211> LENGTH: 120
<212> TYPE: DNA
<213> ORGANISM: Homo sapiens

<400> SEQUENCE: 53
gtgaagtgac aacagcttca gctcgtcatc gatgttatac agaaacacaa aaggaatccc    60
yggcctgtga tgaaggagag gccgttgctg tgtgttcagg acacctcaga gcaggcacat    120

<210> SEQ ID NO 54
<211> LENGTH: 120
<212> TYPE: DNA
<213> ORGANISM: Homo sapiens

<400> SEQUENCE: 54
cagaaacaca aaaggaatcc ccggcctgtg atgaaggaga ggccgttgct gtgtgttcag    60
racacctcag agcaggcaca taaagtgctg gagggtgaca cagcctgtct ggatgtcctc    120

<210> SEQ ID NO 55
<211> LENGTH: 120
<212> TYPE: DNA
<213> ORGANISM: Homo sapiens

```
<400> SEQUENCE: 55
ggagggtgtg ccatccagga ggcgacaccc ccatccagca cacgggccct tccacccgct      60
rtcggtcctg ctaaaggtac gaggctaaaa ccggcctctc cagaaaagaa cgctcagtgt     120

<210> SEQ ID NO 56
<211> LENGTH: 120
<212> TYPE: DNA
<213> ORGANISM: Homo sapiens

<400> SEQUENCE: 56
aaaactgtca tgatgacaaa atgcaagcat gacgtaaaat gcctaggtca gtgcctggca      60
yacagcacat gctgggtaag cgcctgatat tctgatgctg ctctcctccc tacagactct     120

<210> SEQ ID NO 57
<211> LENGTH: 120
<212> TYPE: DNA
<213> ORGANISM: Homo sapiens

<400> SEQUENCE: 57
cttccctcta gccaacaggt gcttttttcac tgccagcatt tctcagcctc caggacaggc     60
ygagtcttgc tcatggctcc cctccctcct ccaggcccac aagctccatg ttggcagtgg    120

<210> SEQ ID NO 58
<211> LENGTH: 120
<212> TYPE: DNA
<213> ORGANISM: Homo sapiens

<400> SEQUENCE: 58
cgttgctgtg tgttcaggac acctcagagc aggcacataa agtgctggag ggtgacacag      60
yctgtctgga tgtcctcggg agggtgtgcc atccaggagg cgacaccccc atccagcaca    120

<210> SEQ ID NO 59
<211> LENGTH: 120
<212> TYPE: DNA
<213> ORGANISM: Homo sapiens

<400> SEQUENCE: 59
aatgtggggt tctcaactgg cctgggaggc agctctgggc acgcccattt cctgagcatg      60
mgactgctct ctgcctcaat ttcctctcct gtgaaatgga gatgctgaca gtaaatactg    120

<210> SEQ ID NO 60
<211> LENGTH: 120
<212> TYPE: DNA
<213> ORGANISM: Homo sapiens

<400> SEQUENCE: 60
cgtaaaatgc ctaggtcagt gcctggcaca cagcacatgc tgggtaagcg cctgatattc      60
ygatgctgct ctcctcccta cagactctct taatcaccag cgtccaaaag gggagaaaaa    120

<210> SEQ ID NO 61
<211> LENGTH: 120
<212> TYPE: DNA
<213> ORGANISM: Homo sapiens

<400> SEQUENCE: 61
gacaatactg agatcatcct caccgagaag aaagtggact cggtatataaat cagatttctg     60 ragcagccgc cgcagcttgg cctgcgtctc ggtggcctct gcaccttgc cactggcgga    120
```

<210> SEQ ID NO 62
<211> LENGTH: 120
<212> TYPE: DNA
<213> ORGANISM: Homo sapiens

<400> SEQUENCE: 62
agggcccagt gtggcccagg tctgggtgct tcctcctccc aaagatcaag tccttcaggg      60
maaccaccta atcctgctcc agaaaacagc agtgtcagac ttctgagggg tcgaggagcg     120

<210> SEQ ID NO 63
<211> LENGTH: 120
<212> TYPE: DNA
<213> ORGANISM: Homo sapiens

<400> SEQUENCE: 63
tgaagagaat acccagctga gcctggaaac caaggcagaa aagcaacacc caggataaca      60
ygccatcaga gtctgcgcaa aggcaccatc acagctctgc tgaaaccagc attttcctgg     120

<210> SEQ ID NO 64
<211> LENGTH: 120
<212> TYPE: DNA
<213> ORGANISM: Homo sapiens

<400> SEQUENCE: 64
aaagcaacac ccaggataac acgccatcag agtctgcgca aaggcaccat cacagctctg      60
ytgaaaccag cattttcctg gcactaaatt acaaacagat tgttgaatg gtccttgaag      120

<210> SEQ ID NO 65
<211> LENGTH: 120
<212> TYPE: DNA
<213> ORGANISM: Homo sapiens

<400> SEQUENCE: 65
agaaatattc atgtggccat ttctgtgggg actctcgtag aatttcagag cctaacattg      60
kaatgcaaca aacagttcct ttcccatctc ctctccggaa cctccttgtc ctggctacaa     120

<210> SEQ ID NO 66
<211> LENGTH: 120
<212> TYPE: DNA
<213> ORGANISM: Homo sapiens

<400> SEQUENCE: 66
gaatggcgag gaaggaccca ggatccatgc tgcctgcgat gttcagagca tcctccttca      60
yccaagctct gatcagctgt cctcctctac tggcttccac ctctggctgc ccttccttcc     120

<210> SEQ ID NO 67
<211> LENGTH: 120
<212> TYPE: DNA
<213> ORGANISM: Homo sapiens

<400> SEQUENCE: 67
cacccaggct ttcttagtca gagatgcaga aatgctgcat gttccatctc ctgctggtga      60
ygtccaaccc acatgaacac accaacatcc gacactcctg caataaaggg gccagtttat     120

<210> SEQ ID NO 68
<211> LENGTH: 120
<212> TYPE: DNA
<213> ORGANISM: Homo sapiens

<400> SEQUENCE: 68

```
tctctgatcc cacgccccac tccgtcaccg tccagcatgg ctggtgtcct cgtcttgcca      60
ytgtctatat gaaatggctc ctggacatgt tcttcactc tgttcctaca gatgccaaca      120
```

<210> SEQ ID NO 69
<211> LENGTH: 120
<212> TYPE: DNA
<213> ORGANISM: Homo sapiens

<400> SEQUENCE: 69

```
cagctatagt aagaattttt tgagaaagat gacaaccaca accaaatgag tctgcaaata      60
ycacagcagg acacacacca tgtaaaccct ggagctgagg aagatgaac aggcacacgg      120
```

<210> SEQ ID NO 70
<211> LENGTH: 120
<212> TYPE: DNA
<213> ORGANISM: Homo sapiens

<400> SEQUENCE: 70

```
agagtagctg aattatttac cttcttcaag aagcactgtc ataggacagg gtttaagact      60
wtaaacctct ggtttaaagt ctggtggtta ctatgctgaa gatagaatct gtatataggt      120
```

<210> SEQ ID NO 71
<211> LENGTH: 120
<212> TYPE: DNA
<213> ORGANISM: Homo sapiens

<400> SEQUENCE: 71

```
gaatttaaca acgtaataat ccctaaagga aaacacactg cctccttctc atctgtcgct      60
wgtccatatg aaaagtagca acgtctggtg gacaagggca gcctcagaat gggctctggg      120
```

<210> SEQ ID NO 72
<211> LENGTH: 120
<212> TYPE: DNA
<213> ORGANISM: Homo sapiens

<400> SEQUENCE: 72

```
cagattccca cacactggac ttcctctgac tggctgatgg cagggatcct ggctttaggc      60
rtgagtatct ttcttctttt gcatcttcct acaatttaca gttttgtat aaatacaatg      120
```

<210> SEQ ID NO 73
<211> LENGTH: 120
<212> TYPE: DNA
<213> ORGANISM: Homo sapiens

<400> SEQUENCE: 73

```
ctcaaggtta cctggctaca aggtgatgaa acagggcttt gaccctagtt tttgttcgtg      60
wctccaaggc catattctta ttgattgagg ggaacaagta tgatttcaga tcctctccta      120
```

<210> SEQ ID NO 74
<211> LENGTH: 120
<212> TYPE: DNA
<213> ORGANISM: Homo sapiens

<400> SEQUENCE: 74

```
cccctaccct agtgtgactc atggccacat aaatgcccca tccccagtgg tgcttcagct      60
stgacccagt ggaaccagtg tcaccggctc agcctccagg tagggactg gcttcccagg      120
```

<210> SEQ ID NO 75

```
<210> SEQ ID NO 75
<211> LENGTH: 22
<212> TYPE: DNA
<213> ORGANISM: Artificial Sequence
<220> FEATURE:
<223> OTHER INFORMATION: Primer

<400> SEQUENCE: 75
gaggtgaaaa tgggaacaaa gg                                              22

<210> SEQ ID NO 76
<211> LENGTH: 22
<212> TYPE: DNA
<213> ORGANISM: Artificial Sequence
<220> FEATURE:
<223> OTHER INFORMATION: Primer

<400> SEQUENCE: 76
aaaactacaa ccaagcctgt cc                                              22

<210> SEQ ID NO 77
<211> LENGTH: 23
<212> TYPE: DNA
<213> ORGANISM: Artificial Sequence
<220> FEATURE:
<223> OTHER INFORMATION: Primer

<400> SEQUENCE: 77
taagccgttt tctgagagag gtg                                             23

<210> SEQ ID NO 78
<211> LENGTH: 22
<212> TYPE: DNA
<213> ORGANISM: Artificial Sequence
<220> FEATURE:
<223> OTHER INFORMATION: Primer

<400> SEQUENCE: 78
ctctttgctc agtctgggat tt                                              22

<210> SEQ ID NO 79
<211> LENGTH: 23
<212> TYPE: DNA
<213> ORGANISM: Artificial Sequence
<220> FEATURE:
<223> OTHER INFORMATION: Primer

<400> SEQUENCE: 79
ggagagaata tgggagtcta gga                                             23

<210> SEQ ID NO 80
<211> LENGTH: 23
<212> TYPE: DNA
<213> ORGANISM: Artificial Sequence
<220> FEATURE:
<223> OTHER INFORMATION: Primer

<400> SEQUENCE: 80
gcatagttag cctttggggt ctc                                             23

<210> SEQ ID NO 81
<211> LENGTH: 23
<212> TYPE: DNA
<213> ORGANISM: Artificial Sequence
<220> FEATURE:
<223> OTHER INFORMATION: Primer

<400> SEQUENCE: 81
```
ttcacatttt tatctggaca ctt               23

<210> SEQ ID NO 82
<211> LENGTH: 23
<212> TYPE: DNA
<213> ORGANISM: Artificial Sequence
<220> FEATURE:
<223> OTHER INFORMATION: Primer

<400> SEQUENCE: 82
acactttaca gtcaaaggca tac               23

<210> SEQ ID NO 83
<211> LENGTH: 24
<212> TYPE: DNA
<213> ORGANISM: Artificial Sequence
<220> FEATURE:
<223> OTHER INFORMATION: Primer

<400> SEQUENCE: 83
catgtttact gaaaatgaga gttt              24

<210> SEQ ID NO 84
<211> LENGTH: 23
<212> TYPE: DNA
<213> ORGANISM: Artificial Sequence
<220> FEATURE:
<223> OTHER INFORMATION: Primer

<400> SEQUENCE: 84
atgataccaa aattgaagac aag               23

<210> SEQ ID NO 85
<211> LENGTH: 21
<212> TYPE: DNA
<213> ORGANISM: Artificial Sequence
<220> FEATURE:
<223> OTHER INFORMATION: Primer

<400> SEQUENCE: 85
gactcctcct atttcatggt c                 21

<210> SEQ ID NO 86
<211> LENGTH: 23
<212> TYPE: DNA
<213> ORGANISM: Artificial Sequence
<220> FEATURE:
<223> OTHER INFORMATION: Primer

<400> SEQUENCE: 86
gccccatact tgatattaga tgt               23

<210> SEQ ID NO 87
<211> LENGTH: 22
<212> TYPE: DNA
<213> ORGANISM: Artificial Sequence
<220> FEATURE:
<223> OTHER INFORMATION: Primer

<400> SEQUENCE: 87
gagaatccaa atgcagatag ag                22

<210> SEQ ID NO 88
<211> LENGTH: 22
<212> TYPE: DNA

```
<213> ORGANISM: Artificial Sequence
<220> FEATURE:
<223> OTHER INFORMATION: Primer

<400> SEQUENCE: 88
atgtttttca gggatagaca aa                                              22

<210> SEQ ID NO 89
<211> LENGTH: 24
<212> TYPE: DNA
<213> ORGANISM: Artificial Sequence
<220> FEATURE:
<223> OTHER INFORMATION: Primer

<400> SEQUENCE: 89
catgtttact gaaaatgaga gttt                                            24

<210> SEQ ID NO 90
<211> LENGTH: 23
<212> TYPE: DNA
<213> ORGANISM: Artificial Sequence
<220> FEATURE:
<223> OTHER INFORMATION: Primer

<400> SEQUENCE: 90
atgataccaa aattgaagac aag                                             23

<210> SEQ ID NO 91
<211> LENGTH: 23
<212> TYPE: DNA
<213> ORGANISM: Artificial Sequence
<220> FEATURE:
<223> OTHER INFORMATION: Primer

<400> SEQUENCE: 91
tccattgtat tcagatttct ctc                                             23

<210> SEQ ID NO 92
<211> LENGTH: 23
<212> TYPE: DNA
<213> ORGANISM: Artificial Sequence
<220> FEATURE:
<223> OTHER INFORMATION: Primer

<400> SEQUENCE: 92
taagcacttt taagcatttt gag                                             23

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93
aaggggtcta aatgaaaaac tt                                              22

<210> SEQ ID NO 94
<211> LENGTH: 23
<212> TYPE: DNA
<213> ORGANISM: Artificial Sequence
<220> FEATURE:
<223> OTHER INFORMATION: Primer

<400> SEQUENCE: 94
cacatgatat tcaaaggaaa tgt                                             23
```

```
<210> SEQ ID NO 95
<211> LENGTH: 23
<212> TYPE: DNA
<213> ORGANISM: Artificial Sequence
<220> FEATURE:
<223> OTHER INFORMATION: Primer

<400> SEQUENCE: 95
aagaacaagg accaagagga cag                                                23

<210> SEQ ID NO 96
<211> LENGTH: 23
<212> TYPE: DNA
<213> ORGANISM: Artificial Sequence
<220> FEATURE:
<223> OTHER INFORMATION: Primer

<400> SEQUENCE: 96
cttgtagagc tcaaaggcat acg                                                23

<210> SEQ ID NO 97
<211> LENGTH: 23
<212> TYPE: DNA
<213> ORGANISM: Artificial Sequence
<220> FEATURE:
<223> OTHER INFORMATION: Primer

<400> SEQUENCE: 97
aggtttattc gacaaagtta agg                                                23

<210> SEQ ID NO 98
<211> LENGTH: 23
<212> TYPE: DNA
<213> ORGANISM: Artificial Sequence
<220> FEATURE:
<223> OTHER INFORMATION: Primer

<400> SEQUENCE: 98
ggttgtctct aaactcaaaa gaa                                                23

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
actgaataat ggccaatgag                                                    20

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
aggttccttg actccaactc                                                    20

<210> SEQ ID NO 101
<211> LENGTH: 21
<212> TYPE: DNA
<213> ORGANISM: Artificial Sequence
<220> FEATURE:
```

<223> OTHER INFORMATION: Primer

<400> SEQUENCE: 101
agcagcataa atggacttct t                                              21

<210> SEQ ID NO 102
<211> LENGTH: 21
<212> TYPE: DNA
<213> ORGANISM: Artificial Sequence
<220> FEATURE:
<223> OTHER INFORMATION: Primer

<400> SEQUENCE: 102
cagttgtggt ggattaatgt t                                              21

<210> SEQ ID NO 103
<211> LENGTH: 20
<212> TYPE: DNA
<213> ORGANISM: Artificial Sequence
<220> FEATURE:
<223> OTHER INFORMATION: Primer

<400> SEQUENCE: 103
tccacacctc aaggtagttc                                                20

<210> SEQ ID NO 104
<211> LENGTH: 20
<212> TYPE: DNA
<213> ORGANISM: Artificial Sequence
<220> FEATURE:
<223> OTHER INFORMATION: Primer

<400> SEQUENCE: 104
gtgaggtgag atcctgaaac                                                20

<210> SEQ ID NO 105
<211> LENGTH: 21
<212> TYPE: DNA
<213> ORGANISM: Artificial Sequence
<220> FEATURE:
<223> OTHER INFORMATION: Primer

<400> SEQUENCE: 105
gactgggaac ctccatagtt a                                              21

<210> SEQ ID NO 106
<211> LENGTH: 23
<212> TYPE: DNA
<213> ORGANISM: Artificial Sequence
<220> FEATURE:
<223> OTHER INFORMATION: Primer

<400> SEQUENCE: 106
gtatcctacg ggacagagtt tat                                            23

<210> SEQ ID NO 107
<211> LENGTH: 22
<212> TYPE: DNA
<213> ORGANISM: Artificial Sequence
<220> FEATURE:
<223> OTHER INFORMATION: Primer

<400> SEQUENCE: 107
gcttttctga tgttttctc at                                              22

```
<210> SEQ ID NO 108
<211> LENGTH: 24
<212> TYPE: DNA
<213> ORGANISM: Artificial Sequence
<220> FEATURE:
<223> OTHER INFORMATION: Primer

<400> SEQUENCE: 108
tctttaatgg atttagtgag tctg                                           24

<210> SEQ ID NO 109
<211> LENGTH: 23
<212> TYPE: DNA
<213> ORGANISM: Artificial Sequence
<220> FEATURE:
<223> OTHER INFORMATION: Primer

<400> SEQUENCE: 109
ggacacagca ttacttctac cta                                            23

<210> SEQ ID NO 110
<211> LENGTH: 22
<212> TYPE: DNA
<213> ORGANISM: Artificial Sequence
<220> FEATURE:
<223> OTHER INFORMATION: Primer

<400> SEQUENCE: 110
actccacaga aaagatcaat gt                                             22

<210> SEQ ID NO 111
<211> LENGTH: 23
<212> TYPE: DNA
<213> ORGANISM: Artificial Sequence
<220> FEATURE:
<223> OTHER INFORMATION: Primer

<400> SEQUENCE: 111
atgctaaggt acccacaaga tgg                                            23

<210> SEQ ID NO 112
<211> LENGTH: 21
<212> TYPE: DNA
<213> ORGANISM: Artificial Sequence
<220> FEATURE:
<223> OTHER INFORMATION: Primer

<400> SEQUENCE: 112
cttcttggcc atgggaattt g                                              21

<210> SEQ ID NO 113
<211> LENGTH: 23
<212> TYPE: DNA
<213> ORGANISM: Artificial Sequence
<220> FEATURE:
<223> OTHER INFORMATION: Primer

<400> SEQUENCE: 113
tttgccacta gatcaagaag tat                                            23

<210> SEQ ID NO 114
<211> LENGTH: 23
<212> TYPE: DNA
<213> ORGANISM: Artificial Sequence
<220> FEATURE:
<223> OTHER INFORMATION: Primer
```

```
<400> SEQUENCE: 114
catactttcc ttcctggtaa ctc                                              23

<210> SEQ ID NO 115
<211> LENGTH: 23
<212> TYPE: DNA
<213> ORGANISM: Artificial Sequence
<220> FEATURE:
<223> OTHER INFORMATION: Primer

<400> SEQUENCE: 115
atcagtacca tgaacaatct cat                                              23

<210> SEQ ID NO 116
<211> LENGTH: 25
<212> TYPE: DNA
<213> ORGANISM: Artificial Sequence
<220> FEATURE:
<223> OTHER INFORMATION: Primer

<400> SEQUENCE: 116
aaaccaaatt aacttaacaa ttcaa                                            25

<210> SEQ ID NO 117
<211> LENGTH: 22
<212> TYPE: DNA
<213> ORGANISM: Artificial Sequence
<220> FEATURE:
<223> OTHER INFORMATION: Primer

<400> SEQUENCE: 117
tagagccctt tggtctttag tc                                               22

<210> SEQ ID NO 118
<211> LENGTH: 21
<212> TYPE: DNA
<213> ORGANISM: Artificial Sequence
<220> FEATURE:
<223> OTHER INFORMATION: Primer

<400> SEQUENCE: 118
ctgggcaaca gaaacttcat c                                                21

<210> SEQ ID NO 119
<211> LENGTH: 23
<212> TYPE: DNA
<213> ORGANISM: Artificial Sequence
<220> FEATURE:
<223> OTHER INFORMATION: Primer

<400> SEQUENCE: 119
cctaacctca gtcaattgtt aaa                                              23

<210> SEQ ID NO 120
<211> LENGTH: 23
<212> TYPE: DNA
<213> ORGANISM: Artificial Sequence
<220> FEATURE:
<223> OTHER INFORMATION: Primer

<400> SEQUENCE: 120
aaatgtgctt accttctcag ata                                              23

<210> SEQ ID NO 121
<211> LENGTH: 22
```

```
<212> TYPE: DNA
<213> ORGANISM: Artificial Sequence
<220> FEATURE:
<223> OTHER INFORMATION: Primer

<400> SEQUENCE: 121
aaacaggctc aggaagagct ta                                              22

<210> SEQ ID NO 122
<211> LENGTH: 23
<212> TYPE: DNA
<213> ORGANISM: Artificial Sequence
<220> FEATURE:
<223> OTHER INFORMATION: Primer

<400> SEQUENCE: 122
ctgccttcag acttcctctt aca                                             23

<210> SEQ ID NO 123
<211> LENGTH: 23
<212> TYPE: DNA
<213> ORGANISM: Artificial Sequence
<220> FEATURE:
<223> OTHER INFORMATION: Primer

<400> SEQUENCE: 123
agtatctaag accaaaggga tgt                                             23

<210> SEQ ID NO 124
<211> LENGTH: 23
<212> TYPE: DNA
<213> ORGANISM: Artificial Sequence
<220> FEATURE:
<223> OTHER INFORMATION: Primer

<400> SEQUENCE: 124
aaagcagtga atatcagaag atg                                             23

<210> SEQ ID NO 125
<211> LENGTH: 22
<212> TYPE: DNA
<213> ORGANISM: Artificial Sequence
<220> FEATURE:
<223> OTHER INFORMATION: Primer

<400> SEQUENCE: 125
gcattacctt ctacaattgg tc                                              22

<210> SEQ ID NO 126
<211> LENGTH: 24
<212> TYPE: DNA
<213> ORGANISM: Artificial Sequence
<220> FEATURE:
<223> OTHER INFORMATION: Primer

<400> SEQUENCE: 126
gtgaagtact aatgtctgca aaac                                            24

<210> SEQ ID NO 127
<211> LENGTH: 23
<212> TYPE: DNA
<213> ORGANISM: Artificial Sequence
<220> FEATURE:
<223> OTHER INFORMATION: Primer

<400> SEQUENCE: 127
```
aaaggataca ccatttctat tca                                              23

<210> SEQ ID NO 128
<211> LENGTH: 24
<212> TYPE: DNA
<213> ORGANISM: Artificial Sequence
<220> FEATURE:
<223> OTHER INFORMATION: Primer

<400> SEQUENCE: 128
tgaggaagaa ctgataaaat gtaa                                             24

<210> SEQ ID NO 129
<211> LENGTH: 24
<212> TYPE: DNA
<213> ORGANISM: Artificial Sequence
<220> FEATURE:
<223> OTHER INFORMATION: Primer

<400> SEQUENCE: 129
gcataggttc tacatgtttt atgt                                             24

<210> SEQ ID NO 130
<211> LENGTH: 23
<212> TYPE: DNA
<213> ORGANISM: Artificial Sequence
<220> FEATURE:
<223> OTHER INFORMATION: Primer

<400> SEQUENCE: 130
aatcagaaaa gtgaaggaaa act                                              23

<210> SEQ ID NO 131
<211> LENGTH: 23
<212> TYPE: DNA
<213> ORGANISM: Artificial Sequence
<220> FEATURE:
<223> OTHER INFORMATION: Primer

<400> SEQUENCE: 131
ctcttttcct acctgaactc ttc                                              23

<210> SEQ ID NO 132
<211> LENGTH: 23
<212> TYPE: DNA
<213> ORGANISM: Artificial Sequence
<220> FEATURE:
<223> OTHER INFORMATION: Primer

<400> SEQUENCE: 132
taaacccaga tgaaaataga tgt                                              23

<210> SEQ ID NO 133
<211> LENGTH: 23
<212> TYPE: DNA
<213> ORGANISM: Artificial Sequence
<220> FEATURE:
<223> OTHER INFORMATION: Primer

<400> SEQUENCE: 133
agtgaaggga aaagagtaat gat                                              23

<210> SEQ ID NO 134
<211> LENGTH: 23
<212> TYPE: DNA
<213> ORGANISM: Artificial Sequence

```
<220> FEATURE:
<223> OTHER INFORMATION: Primer

<400> SEQUENCE: 134
ttaagtctca gatggaatgt ctc                                              23

<210> SEQ ID NO 135
<211> LENGTH: 21
<212> TYPE: DNA
<213> ORGANISM: Artificial Sequence
<220> FEATURE:
<223> OTHER INFORMATION: Primer

<400> SEQUENCE: 135
ctaacttgca cttcctcctc t                                                21

<210> SEQ ID NO 136
<211> LENGTH: 23
<212> TYPE: DNA
<213> ORGANISM: Artificial Sequence
<220> FEATURE:
<223> OTHER INFORMATION: Primer

<400> SEQUENCE: 136
aggacactac agtttctcta tgc                                              23

<210> SEQ ID NO 137
<211> LENGTH: 23
<212> TYPE: DNA
<213> ORGANISM: Artificial Sequence
<220> FEATURE:
<223> OTHER INFORMATION: Primer

<400> SEQUENCE: 137
catcatccag gataagtaca cac                                              23

<210> SEQ ID NO 138
<211> LENGTH: 21
<212> TYPE: DNA
<213> ORGANISM: Artificial Sequence
<220> FEATURE:
<223> OTHER INFORMATION: Primer

<400> SEQUENCE: 138
ttctgttcat cttcccagaa t                                                21

<210> SEQ ID NO 139
<211> LENGTH: 22
<212> TYPE: DNA
<213> ORGANISM: Artificial Sequence
<220> FEATURE:
<223> OTHER INFORMATION: Primer

<400> SEQUENCE: 139
ggtatcatgg taaccacaag tt                                               22

<210> SEQ ID NO 140
<211> LENGTH: 23
<212> TYPE: DNA
<213> ORGANISM: Artificial Sequence
<220> FEATURE:
<223> OTHER INFORMATION: Primer

<400> SEQUENCE: 140
aatcgtcctg tctttattct ttt                                              23
```

<210> SEQ ID NO 141
<211> LENGTH: 23
<212> TYPE: DNA
<213> ORGANISM: Artificial Sequence
<220> FEATURE:
<223> OTHER INFORMATION: Primer

<400> SEQUENCE: 141
taggtttgac tgttgcatta ttt                                          23

<210> SEQ ID NO 142
<211> LENGTH: 23
<212> TYPE: DNA
<213> ORGANISM: Artificial Sequence
<220> FEATURE:
<223> OTHER INFORMATION: Primer

<400> SEQUENCE: 142
aatttcacag agggtaaaat agg                                          23

<210> SEQ ID NO 143
<211> LENGTH: 23
<212> TYPE: DNA
<213> ORGANISM: Artificial Sequence
<220> FEATURE:
<223> OTHER INFORMATION: Primer

<400> SEQUENCE: 143
tattctgaag caaatccaag ata                                          23

<210> SEQ ID NO 144
<211> LENGTH: 22
<212> TYPE: DNA
<213> ORGANISM: Artificial Sequence
<220> FEATURE:
<223> OTHER INFORMATION: Primer

<400> SEQUENCE: 144
agtcacaata tgtggaccat tt                                           22

<210> SEQ ID NO 145
<211> LENGTH: 23
<212> TYPE: DNA
<213> ORGANISM: Artificial Sequence
<220> FEATURE:
<223> OTHER INFORMATION: Primer

<400> SEQUENCE: 145
caattactct gtgttgggtc tac                                          23

<210> SEQ ID NO 146
<211> LENGTH: 23
<212> TYPE: DNA
<213> ORGANISM: Artificial Sequence
<220> FEATURE:
<223> OTHER INFORMATION: Primer

<400> SEQUENCE: 146
tcatctttcc actttctcta ttg                                          23

<210> SEQ ID NO 147
<211> LENGTH: 23
<212> TYPE: DNA
<213> ORGANISM: Artificial Sequence
<220> FEATURE:
<223> OTHER INFORMATION: Primer

<400> SEQUENCE: 147
atagattttg ggtaaagcag att                                              23

<210> SEQ ID NO 148
<211> LENGTH: 23
<212> TYPE: DNA
<213> ORGANISM: Artificial Sequence
<220> FEATURE:
<223> OTHER INFORMATION: Primer

<400> SEQUENCE: 148
ttggcagaga gagatttatt tta                                              23

<210> SEQ ID NO 149
<211> LENGTH: 23
<212> TYPE: DNA
<213> ORGANISM: Artificial Sequence
<220> FEATURE:
<223> OTHER INFORMATION: Primer

<400> SEQUENCE: 149
tcgatgttat acagaaacac aaa                                              23

<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
acacactgag cgttcttttc                                                  20

<210> SEQ ID NO 151
<211> LENGTH: 20
<212> TYPE: DNA
<213> ORGANISM: Artificial Sequence
<220> FEATURE:
<223> OTHER INFORMATION: Primer

<400> SEQUENCE: 151
agaatgtggg gttctcaact                                                  20

<210> SEQ ID NO 152
<211> LENGTH: 23
<212> TYPE: DNA
<213> ORGANISM: Artificial Sequence
<220> FEATURE:
<223> OTHER INFORMATION: Primer

<400> SEQUENCE: 152
attaagagag tctgtaggga gga                                              23

<210> SEQ ID NO 153
<211> LENGTH: 20
<212> TYPE: DNA
<213> ORGANISM: Artificial Sequence
<220> FEATURE:
<223> OTHER INFORMATION: Primer

<400> SEQUENCE: 153
atactgtcct gagcctgcta                                                  20

<210> SEQ ID NO 154

```
<211> LENGTH: 22
<212> TYPE: DNA
<213> ORGANISM: Artificial Sequence
<220> FEATURE:
<223> OTHER INFORMATION: Primer

<400> SEQUENCE: 154
aagtctgaca ctgctgtttt ct                                              22

<210> SEQ ID NO 155
<211> LENGTH: 23
<212> TYPE: DNA
<213> ORGANISM: Artificial Sequence
<220> FEATURE:
<223> OTHER INFORMATION: Primer

<400> SEQUENCE: 155
tcgatgttat acagaaacac aaa                                             23

<210> SEQ ID NO 156
<211> LENGTH: 20
<212> TYPE: DNA
<213> ORGANISM: Artificial Sequence
<220> FEATURE:
<223> OTHER INFORMATION: Primer

<400> SEQUENCE: 156
acacactgag cgttcttttc                                                 20

<210> SEQ ID NO 157
<211> LENGTH: 23
<212> TYPE: DNA
<213> ORGANISM: Artificial Sequence
<220> FEATURE:
<223> OTHER INFORMATION: Primer

<400> SEQUENCE: 157
aagggagaca atactgagat cat                                             23

<210> SEQ ID NO 158
<211> LENGTH: 20
<212> TYPE: DNA
<213> ORGANISM: Artificial Sequence
<220> FEATURE:
<223> OTHER INFORMATION: Primer

<400> SEQUENCE: 158
ctttgacttt cccacttgaa                                                 20

<210> SEQ ID NO 159
<211> LENGTH: 20
<212> TYPE: DNA
<213> ORGANISM: Artificial Sequence
<220> FEATURE:
<223> OTHER INFORMATION: Primer

<400> SEQUENCE: 159
atactgtcct gagcctgcta                                                 20

<210> SEQ ID NO 160
<211> LENGTH: 22
<212> TYPE: DNA
<213> ORGANISM: Artificial Sequence
<220> FEATURE:
<223> OTHER INFORMATION: Primer

<400> SEQUENCE: 160
```

```
aagtctgaca ctgctgtttt ct                                        22
```

<210> SEQ ID NO 161
<211> LENGTH: 23
<212> TYPE: DNA
<213> ORGANISM: Artificial Sequence
<220> FEATURE:
<223> OTHER INFORMATION: Primer

<400> SEQUENCE: 161

```
ggtgtagggt agcttgagat cag                                       23
```

<210> SEQ ID NO 162
<211> LENGTH: 22
<212> TYPE: DNA
<213> ORGANISM: Artificial Sequence
<220> FEATURE:
<223> OTHER INFORMATION: Primer

<400> SEQUENCE: 162

```
aaaagaacag aagggacgaa gg                                        22
```

<210> SEQ ID NO 163
<211> LENGTH: 22
<212> TYPE: DNA
<213> ORGANISM: Artificial Sequence
<220> FEATURE:
<223> OTHER INFORMATION: Primer

<400> SEQUENCE: 163

```
aactcacagt accacctttc ag                                        22
```

<210> SEQ ID NO 164
<211> LENGTH: 23
<212> TYPE: DNA
<213> ORGANISM: Artificial Sequence
<220> FEATURE:
<223> OTHER INFORMATION: Primer

<400> SEQUENCE: 164

```
gatgtaacaa gaacaaagtg gtc                                       23
```

<210> SEQ ID NO 165
<211> LENGTH: 23
<212> TYPE: DNA
<213> ORGANISM: Artificial Sequence
<220> FEATURE:
<223> OTHER INFORMATION: Primer

<400> SEQUENCE: 165

```
gttcttgtta catccagcaa tag                                       23
```

<210> SEQ ID NO 166
<211> LENGTH: 23
<212> TYPE: DNA
<213> ORGANISM: Artificial Sequence
<220> FEATURE:
<223> OTHER INFORMATION: Primer

<400> SEQUENCE: 166

```
ggtgtcaaag tcagagagag taa                                       23
```

<210> SEQ ID NO 167
<211> LENGTH: 24
<212> TYPE: DNA

<213> ORGANISM: Artificial Sequence
<220> FEATURE:
<223> OTHER INFORMATION: Primer

<400> SEQUENCE: 167
tcagactaga atatttttca cagc                                              24

<210> SEQ ID NO 168
<211> LENGTH: 20
<212> TYPE: DNA
<213> ORGANISM: Artificial Sequence
<220> FEATURE:
<223> OTHER INFORMATION: Primer

<400> SEQUENCE: 168
tgtccctgaa ttagccatag                                                   20

<210> SEQ ID NO 169
<211> LENGTH: 23
<212> TYPE: DNA
<213> ORGANISM: Artificial Sequence
<220> FEATURE:
<223> OTHER INFORMATION: Primer

<400> SEQUENCE: 169
gctgaattat ttaccttctt caa                                               23

<210> SEQ ID NO 170
<211> LENGTH: 23
<212> TYPE: DNA
<213> ORGANISM: Artificial Sequence
<220> FEATURE:
<223> OTHER INFORMATION: Primer

<400> SEQUENCE: 170
aatctttatg atgcactgtg tct                                               23

<210> SEQ ID NO 171
<211> LENGTH: 23
<212> TYPE: DNA
<213> ORGANISM: Artificial Sequence
<220> FEATURE:
<223> OTHER INFORMATION: Primer

<400> SEQUENCE: 171
ggatcgaatt taacaacgta ata                                               23

<210> SEQ ID NO 172
<211> LENGTH: 24
<212> TYPE: DNA
<213> ORGANISM: Artificial Sequence
<220> FEATURE:
<223> OTHER INFORMATION: Primer

<400> SEQUENCE: 172
caaaaactgt aaattgtagg aaga                                              24

<210> SEQ ID NO 173
<211> LENGTH: 23
<212> TYPE: DNA
<213> ORGANISM: Artificial Sequence
<220> FEATURE:
<223> OTHER INFORMATION: Primer

<400> SEQUENCE: 173
tggagataca gagatcttag gtg                                               23

<210> SEQ ID NO 174
<211> LENGTH: 21
<212> TYPE: DNA
<213> ORGANISM: Artificial Sequence
<220> FEATURE:
<223> OTHER INFORMATION: Primer

<400> SEQUENCE: 174
gaagcaatag caaagactcc t                                              21

<210> SEQ ID NO 175
<211> LENGTH: 21
<212> TYPE: DNA
<213> ORGANISM: Artificial Sequence
<220> FEATURE:
<223> OTHER INFORMATION: Primer

<400> SEQUENCE: 175
caacaatctt cctgtgactt g                                              21

<210> SEQ ID NO 176
<211> LENGTH: 20
<212> TYPE: DNA
<213> ORGANISM: Artificial Sequence
<220> FEATURE:
<223> OTHER INFORMATION: Primer

<400> SEQUENCE: 176
gctcttgtac cttcccaatc                                                20

<210> SEQ ID NO 177
<211> LENGTH: 23
<212> TYPE: DNA
<213> ORGANISM: Artificial Sequence
<220> FEATURE:
<223> OTHER INFORMATION: Primer

<400> SEQUENCE: 177
ccagtactgg ctgtctttcc aaa                                            23

<210> SEQ ID NO 178
<211> LENGTH: 26
<212> TYPE: DNA
<213> ORGANISM: Artificial Sequence
<220> FEATURE:
<223> OTHER INFORMATION: Primer

<400> SEQUENCE: 178
gcagtgttat ctgtgatcta cctaca                                         26

<210> SEQ ID NO 179
<211> LENGTH: 25
<212> TYPE: DNA
<213> ORGANISM: Artificial Sequence
<220> FEATURE:
<223> OTHER INFORMATION: Primer

<400> SEQUENCE: 179
gtggtgatgt tgatgatgat aatga                                          25

<210> SEQ ID NO 180
<211> LENGTH: 25
<212> TYPE: DNA
<213> ORGANISM: Artificial Sequence
<220> FEATURE:

<223> OTHER INFORMATION: Primer

<400> SEQUENCE: 180
cctctgctga tcagaaaggt tattt                                          25

<210> SEQ ID NO 181
<211> LENGTH: 27
<212> TYPE: DNA
<213> ORGANISM: Artificial Sequence
<220> FEATURE:
<223> OTHER INFORMATION: Primer

<400> SEQUENCE: 181
aaaagatcac cagtgtaaaa cgtaagg                                        27

<210> SEQ ID NO 182
<211> LENGTH: 26
<212> TYPE: DNA
<213> ORGANISM: Artificial Sequence
<220> FEATURE:
<223> OTHER INFORMATION: Primer

<400> SEQUENCE: 182
ctcaaactca tgatgaccta cctgaa                                         26

<210> SEQ ID NO 183
<211> LENGTH: 18
<212> TYPE: DNA
<213> ORGANISM: Artificial Sequence
<220> FEATURE:
<223> OTHER INFORMATION: Primer

<400> SEQUENCE: 183
ctgtcctggg tgcacaca                                                  18

<210> SEQ ID NO 184
<211> LENGTH: 23
<212> TYPE: DNA
<213> ORGANISM: Artificial Sequence
<220> FEATURE:
<223> OTHER INFORMATION: Primer

<400> SEQUENCE: 184
gctctgcact gaccagaaga aag                                            23

<210> SEQ ID NO 185
<211> LENGTH: 32
<212> TYPE: DNA
<213> ORGANISM: Artificial Sequence
<220> FEATURE:
<223> OTHER INFORMATION: Primer

<400> SEQUENCE: 185
tcaagccata tacagaaaat actgaagtaa tg                                  32

<210> SEQ ID NO 186
<211> LENGTH: 28
<212> TYPE: DNA
<213> ORGANISM: Artificial Sequence
<220> FEATURE:
<223> OTHER INFORMATION: Primer

<400> SEQUENCE: 186
gcctggtttt atacatttta gggagaca                                       28

<210> SEQ ID NO 187
<211> LENGTH: 17
<212> TYPE: DNA
<213> ORGANISM: Artificial Sequence
<220> FEATURE:
<223> OTHER INFORMATION: Primer

<400> SEQUENCE: 187
tggaagcccc agcaggt                                                  17

<210> SEQ ID NO 188
<211> LENGTH: 22
<212> TYPE: DNA
<213> ORGANISM: Artificial Sequence
<220> FEATURE:
<223> OTHER INFORMATION: Primer

<400> SEQUENCE: 188
tgatgctgtg tccgtttcta gg                                            22

<210> SEQ ID NO 189
<211> LENGTH: 24
<212> TYPE: DNA
<213> ORGANISM: Artificial Sequence
<220> FEATURE:
<223> OTHER INFORMATION: Primer

<400> SEQUENCE: 189
ggcgtcttca gttttcaact tcac                                          24

<210> SEQ ID NO 190
<211> LENGTH: 23
<212> TYPE: DNA
<213> ORGANISM: Artificial Sequence
<220> FEATURE:
<223> OTHER INFORMATION: Primer

<400> SEQUENCE: 190
agctgctgtg attagggaaa cat                                           23

<210> SEQ ID NO 191
<211> LENGTH: 20
<212> TYPE: DNA
<213> ORGANISM: Artificial Sequence
<220> FEATURE:
<223> OTHER INFORMATION: Primer

<400> SEQUENCE: 191
gctgtccgtg tgacttacca                                               20

<210> SEQ ID NO 192
<211> LENGTH: 26
<212> TYPE: DNA
<213> ORGANISM: Artificial Sequence
<220> FEATURE:
<223> OTHER INFORMATION: Primer

<400> SEQUENCE: 192
actggattga agaaagaggc atagac                                        26

<210> SEQ ID NO 193
<211> LENGTH: 22
<212> TYPE: DNA
<213> ORGANISM: Artificial Sequence
<220> FEATURE:
<223> OTHER INFORMATION: Primer

<400> SEQUENCE: 193
ggcagtgaca actcgtttga ca                                          22

<210> SEQ ID NO 194
<211> LENGTH: 21
<212> TYPE: DNA
<213> ORGANISM: Artificial Sequence
<220> FEATURE:
<223> OTHER INFORMATION: Primer

<400> SEQUENCE: 194
gcaggatctt ttcgtgcaac c                                           21

<210> SEQ ID NO 195
<211> LENGTH: 34
<212> TYPE: DNA
<213> ORGANISM: Artificial Sequence
<220> FEATURE:
<223> OTHER INFORMATION: Primer

<400> SEQUENCE: 195
aattgtttcc agttttgatt gtgattatat gaaa                             34

<210> SEQ ID NO 196
<211> LENGTH: 24
<212> TYPE: DNA
<213> ORGANISM: Artificial Sequence
<220> FEATURE:
<223> OTHER INFORMATION: Primer

<400> SEQUENCE: 196
gaacaaaggg catttgatga caac                                        24

<210> SEQ ID NO 197
<211> LENGTH: 26
<212> TYPE: DNA
<213> ORGANISM: Artificial Sequence
<220> FEATURE:
<223> OTHER INFORMATION: Primer

<400> SEQUENCE: 197
acagaaaagc acagagaaca atgaaa                                      26

<210> SEQ ID NO 198
<211> LENGTH: 39
<212> TYPE: DNA
<213> ORGANISM: Artificial Sequence
<220> FEATURE:
<223> OTHER INFORMATION: Primer

<400> SEQUENCE: 198
atgacctaat tgtctttaaa aaatcaaata ttactgtaa                        39

<210> SEQ ID NO 199
<211> LENGTH: 25
<212> TYPE: DNA
<213> ORGANISM: Artificial Sequence
<220> FEATURE:
<223> OTHER INFORMATION: Primer

<400> SEQUENCE: 199
tgtctgtggc attggagaat attct                                       25

<210> SEQ ID NO 200
<211> LENGTH: 31

```
<212> TYPE: DNA
<213> ORGANISM: Artificial Sequence
<220> FEATURE:
<223> OTHER INFORMATION: Primer

<400> SEQUENCE: 200
acaataagga agtcattagt ctgtttaaac c                                    31

<210> SEQ ID NO 201
<211> LENGTH: 24
<212> TYPE: DNA
<213> ORGANISM: Artificial Sequence
<220> FEATURE:
<223> OTHER INFORMATION: Primer

<400> SEQUENCE: 201
gcctcagagt aagatcttca ggga                                            24

<210> SEQ ID NO 202
<211> LENGTH: 17
<212> TYPE: DNA
<213> ORGANISM: Artificial Sequence
<220> FEATURE:
<223> OTHER INFORMATION: Primer

<400> SEQUENCE: 202
ccctactgcc ccgacct                                                    17

<210> SEQ ID NO 203
<211> LENGTH: 16
<212> TYPE: DNA
<213> ORGANISM: Artificial Sequence
<220> FEATURE:
<223> OTHER INFORMATION: Primer

<400> SEQUENCE: 203
ctggctccca gcctcg                                                     16

<210> SEQ ID NO 204
<211> LENGTH: 29
<212> TYPE: DNA
<213> ORGANISM: Artificial Sequence
<220> FEATURE:
<223> OTHER INFORMATION: Primer

<400> SEQUENCE: 204 aattaccccta tctcgtgtat cttgttaca                                      29

<210> SEQ ID NO 205
<211> LENGTH: 26
<212> TYPE: DNA
<213> ORGANISM: Artificial Sequence
<220> FEATURE:
<223> OTHER INFORMATION: Primer

<400> SEQUENCE: 205
catgtagttg ggagatacag gaatta                                          26

<210> SEQ ID NO 206
<211> LENGTH: 38
<212> TYPE: DNA
<213> ORGANISM: Artificial Sequence
<220> FEATURE:
<223> OTHER INFORMATION: Primer

<400> SEQUENCE: 206
```

-continued tcttaaaatt tatcaaatag tcaattgtca aatttcca                                38

<210> SEQ ID NO 207
<211> LENGTH: 25
<212> TYPE: DNA
<213> ORGANISM: Artificial Sequence
<220> FEATURE:
<223> OTHER INFORMATION: Primer

<400> SEQUENCE: 207
ctccgcaagt gaaaattatc tccaa                                              25

<210> SEQ ID NO 208
<211> LENGTH: 20
<212> TYPE: DNA
<213> ORGANISM: Artificial Sequence
<220> FEATURE:
<223> OTHER INFORMATION: Primer

<400> SEQUENCE: 208
gccgcaacat cagctcttcc                                                    20

<210> SEQ ID NO 209
<211> LENGTH: 28
<212> TYPE: DNA
<213> ORGANISM: Artificial Sequence
<220> FEATURE:
<223> OTHER INFORMATION: Primer

<400> SEQUENCE: 209
tgttatacag aaacacaaaa ggaatccc                                           28

<210> SEQ ID NO 210
<211> LENGTH: 20
<212> TYPE: DNA
<213> ORGANISM: Artificial Sequence
<220> FEATURE:
<223> OTHER INFORMATION: Primer

<400> SEQUENCE: 210
cctctccttc atcacaggcc                                                    20

<210> SEQ ID NO 211
<211> LENGTH: 23
<212> TYPE: DNA
<213> ORGANISM: Artificial Sequence
<220> FEATURE:
<223> OTHER INFORMATION: Primer

<400> SEQUENCE: 211
cgactgctct ctgcctcaat ttc                                                23

<210> SEQ ID NO 212
<211> LENGTH: 23
<212> TYPE: DNA
<213> ORGANISM: Artificial Sequence
<220> FEATURE:
<223> OTHER INFORMATION: Primer

<400> SEQUENCE: 212
cagcatctcc atttcacagg aga                                                23

<210> SEQ ID NO 213
<211> LENGTH: 17
<212> TYPE: DNA
<213> ORGANISM: Artificial Sequence

```
<220> FEATURE:
<223> OTHER INFORMATION: Primer

<400> SEQUENCE: 213
cagcctccag gacaggc                                                  17

<210> SEQ ID NO 214
<211> LENGTH: 20
<212> TYPE: DNA
<213> ORGANISM: Artificial Sequence
<220> FEATURE:
<223> OTHER INFORMATION: Primer

<400> SEQUENCE: 214
gggagccatg agcaagactc                                               20

<210> SEQ ID NO 215
<211> LENGTH: 19
<212> TYPE: DNA
<213> ORGANISM: Artificial Sequence
<220> FEATURE:
<223> OTHER INFORMATION: Primer

<400> SEQUENCE: 215
gtgctggagg gtgacacag                                                19

<210> SEQ ID NO 216
<211> LENGTH: 19
<212> TYPE: DNA
<213> ORGANISM: Artificial Sequence
<220> FEATURE:
<223> OTHER INFORMATION: Primer

<400> SEQUENCE: 216
cccgaggaca tccagacag                                                19

<210> SEQ ID NO 217
<211> LENGTH: 27
<212> TYPE: DNA
<213> ORGANISM: Artificial Sequence
<220> FEATURE:
<223> OTHER INFORMATION: Primer

<400> SEQUENCE: 217
gtggactcgg tataaatcag atttctg                                       27

<210> SEQ ID NO 218
<211> LENGTH: 21
<212> TYPE: DNA
<213> ORGANISM: Artificial Sequence
<220> FEATURE:
<223> OTHER INFORMATION: Primer

<400> SEQUENCE: 218
ctggagcagg attaggtggt t                                             21

<210> SEQ ID NO 219
<211> LENGTH: 20
<212> TYPE: DNA
<213> ORGANISM: Artificial Sequence
<220> FEATURE:
<223> OTHER INFORMATION: Primer

<400> SEQUENCE: 219
gttccatctc ctgctggtga                                               20
```

```
<210> SEQ ID NO 220
<211> LENGTH: 21
<212> TYPE: DNA
<213> ORGANISM: Artificial Sequence
<220> FEATURE:
<223> OTHER INFORMATION: Primer

<400> SEQUENCE: 220
gtgtgttcat gtgggttgga c                                          21

<210> SEQ ID NO 221
<211> LENGTH: 20
<212> TYPE: DNA
<213> ORGANISM: Artificial Sequence
<220> FEATURE:
<223> OTHER INFORMATION: Primer

<400> SEQUENCE: 221
ctggtgtcct cgtcttgcca                                            20

<210> SEQ ID NO 222
<211> LENGTH: 25
<212> TYPE: DNA
<213> ORGANISM: Artificial Sequence
<220> FEATURE:
<223> OTHER INFORMATION: Primer

<400> SEQUENCE: 222
gtccaggagc catttcatat agaca                                      25

<210> SEQ ID NO 223
<211> LENGTH: 25
<212> TYPE: DNA
<213> ORGANISM: Artificial Sequence
<220> FEATURE:
<223> OTHER INFORMATION: Primer

<400> SEQUENCE: 223
ccacaaccaa atgagtctgc aaata                                      25

<210> SEQ ID NO 224
<211> LENGTH: 14
<212> TYPE: DNA
<213> ORGANISM: Artificial Sequence
<220> FEATURE:
<223> OTHER INFORMATION: Primer

<400> SEQUENCE: 224
tggtgtgtgt cctg                                                  14

<210> SEQ ID NO 225
<211> LENGTH: 25
<212> TYPE: DNA
<213> ORGANISM: Artificial Sequence
<220> FEATURE:
<223> OTHER INFORMATION: Primer

<400> SEQUENCE: 225
ctgtcatagg acagggttta agact                                      25

<210> SEQ ID NO 226
<211> LENGTH: 26
<212> TYPE: DNA
<213> ORGANISM: Artificial Sequence
<220> FEATURE:
<223> OTHER INFORMATION: Primer
```

```
<400> SEQUENCE: 226
ccaccagact ttaaaccaga ggttta                                          26

<210> SEQ ID NO 227
<211> LENGTH: 28
<212> TYPE: DNA
<213> ORGANISM: Artificial Sequence
<220> FEATURE:
<223> OTHER INFORMATION: Primer

<400> SEQUENCE: 227
ggaagatgca aagaaagaaa gatactca                                        28

<210> SEQ ID NO 228
<211> LENGTH: 25
<212> TYPE: DNA
<213> ORGANISM: Artificial Sequence
<220> FEATURE:
<223> OTHER INFORMATION: Primer

<400> SEQUENCE: 228
gctttgaccc tagtttttgt tcgtg                                           25

<210> SEQ ID NO 229
<211> LENGTH: 28
<212> TYPE: DNA
<213> ORGANISM: Artificial Sequence
<220> FEATURE:
<223> OTHER INFORMATION: Primer

<400> SEQUENCE: 229
ctcaatcaat aagaatatgg ccttggag                                        28

<210> SEQ ID NO 230
<211> LENGTH: 18
<212> TYPE: DNA
<213> ORGANISM: Artificial Sequence
<220> FEATURE:
<223> OTHER INFORMATION: Primer

<400> SEQUENCE: 230
cccagtggtg cttcagct                                                   18
```